US006015703A

United States Patent [19]
White et al.

[11] Patent Number: 6,015,703
[45] Date of Patent: Jan. 18, 2000

[54] GENETIC CONSTRUCTS AND GENETICALLY MODIFIED MICROBES FOR ENHANCED PRODUCTION OF BETA-GLUCOSIDASE

[75] Inventors: Theresa C. White; Christopher D. Hindle, both of Ottawa, Canada

[73] Assignee: Iogen Corporation, Ottawa, Canada

[21] Appl. No.: 09/037,524

[22] Filed: Mar. 10, 1998

[51] Int. Cl.[7] .............................. C12N 9/42; C12N 1/14; C12N 15/00; C07H 21/04
[52] U.S. Cl. ................ 435/209; 435/254.11; 435/254.3; 435/254.6; 435/254.7; 435/320.1; 536/23.2
[58] Field of Search ................................ 435/209, 320.1, 435/254.3, 254.6, 254.7, 254.11; 536/23.2

[56] References Cited

U.S. PATENT DOCUMENTS

| | | | |
|---|---|---|---|
| 4,464,471 | 8/1984 | Armentrout et al. | 435/253 |
| 4,487,831 | 12/1984 | Day et al. | 435/99 |
| 5,679,543 | 10/1997 | Lawlis | 435/69.1 |
| 5,861,280 | 1/1999 | Lehmbeck | 435/69.1 |
| 5,863,783 | 1/1999 | Van Heuvel et al. | 435/200 |
| 5,874,293 | 2/1999 | Miettinen-Oinonen et al. | 435/263 |
| 5,922,561 | 7/1999 | Thompson et al. | 435/69.1 |

FOREIGN PATENT DOCUMENTS

WO 92/10581 of 1992 WIPO.
WO 98/45455 10/1998 WIPO.

OTHER PUBLICATIONS

Deane et al., "Transformation of *Trichoderma reesei* With A Constitutively Expressed Heterologous Fungal Chitinase Gene", *Enzyme and Microbial Technology*, vol. 24, pp. 419–424, (1999).

Nevalainen et al., "The Molecular Biology of Trichoderma and Its Application To the Expression of Both Homologous and Heterlogous Genes", In: *Molecular Industrial Mycology Systems and Application for Filamentous Fungi*, pp. 129–148, (1991).

Ulhoa et al., "Transformation of Trichoderma Species With Dominant Selectable Markers", *Current Genetics*, vol. 21, pp. 23–26 (1992).

Calmels et al., "High Efficiency Transformation of *Tolypocladium geodes* Conidiospores To Phleomycin Resistance", *Current Genetics*, vol. 20, pp. 309–314, (1991).

Penttila et al., "A Versatile Transformation System for the Cellulolytic Fungus Trichoderma ressei,", *Gene*, 6:155–164, (1987).

Yelton et al., "Transformation of *Aspergillus nidulans* Using A trpC Plasmid", *Proc. Natl. Acad. Sci. USA*, 81:1470–1474, (1984).

Bajar et al., "Identification of a Fungal Cutinase Promoter That is Inducible By a Plant Signal Via a Phosphorylated Transacting Factor," *Proc. Natl. Acad. Sci. USA*, 88:8202–8212, (1991).

Hopwood et al., "Genetic Manipulation of *Streptomyces:* A Laboratory Manual," *The John Innes Foundation*, Norwich, UK, (1985).

(List continued on next page.)

*Primary Examiner*—Robert A. Wax
*Attorney, Agent, or Firm*—Fitzpatrick, Cella, Harper & Scinto

[57] ABSTRACT

This invention relates to the genetic modification of a microbe to enhance its production of an enzyme, beta-glucosidase, that is important in the cellulose conversion process. The inventors have discovered genetic constructs that, when expressed in recombinant microbes, dramatically increase the amount of beta-glucosidase produced relative to untransformed microbes. The genetic constructs comprise a promoter, a xylanase secretion signal, and a mature beta-glucosidase coding region. The increased level of beta-glucosidase significantly increases the efficiency of hydrolysis of cellulose to glucose by cellulase enzymes, thereby enhancing the production of fuel ethanol from cellulose.

29 Claims, 4 Drawing Sheets

OTHER PUBLICATIONS

Brigidi et al., "Genetic Transformation of Intact Cells of *Bacillus subtilis* by Electroporation", *FEMS Microbiol. Lett.*, 55:135–138, (1990).

Sambrook et al., "Molecular Cloning: A Laboratory Manual, Second Edition", *Cold Spring Harbor Press*, P. C1, (1989).

Viera et al., "Production of Single–Straded Plasmid DNA", *Methods Enzymol.*, 153:3, (1987).

Shoemaker et al., "Molecular Cloning of Exo–Cellobiohydrolase 1 Derived from *Trichoderma reesei* Strain L27", *Bio/Technology*, 1:691–696, (1983).

Saarelainen et al., "Cloning, Sequencing and Enhanced Expression of the *Trichoderma reesei* Endoxylanase II (pI 9) Gene xln2", *Mol. Gen. Genet.*, 241:497–503, (1993).

Vanhanen et al., "Isolation and Characterization of the 3–Phosphoglycerate Kinase Gene (pgk) from the Filamentous Fungus Trichoderma reesei ", Curr. Genet., 15:181–186, (1989).

Ghose, "Measurement of Cellulase Activities", *Pure and Appl. Chem.*, 59:257–268, (1987).

Carter et al., "Chromosomal and Genetic Analysis of the Electrophoretic Karotype of *Trichoderma reesei:* Mapping of the Cellulase and Xylanase Genes", *Molecular Microbiology*, 6:2167–2174, (1992).

Grethlein, "Chemical Breakdown of Cellulosic Materials", *J. Appl. Chem. Biotechnol*, 28:296–308, (1978).

Montenecourt et al., "Selective Screening Methods for the Isolation of High Yielding Cellulase Mutants of T. ressei,", *Adv. Chem. Ser.* 181:289–301: (1979).

Mandels et al., "Induction of Cellulase in *Trichoderma viride* as Influenced by Carbon Sources and Metals", *J. Bacteriol.*, 73:269–278, (1957).

Van den Elzen et al., "A Chimaeric Hygromycin Reisstance Gene as a Selectable Marker in Plant Cells", *Plant Mol. Biol.*, 5:299–302, (1989).

Kawaguchi, T., et al., "Cloning and Sequencing of the cDNA Encoding Beta–Glucosidase 1 from *Aspergillus Aculeatus*", *Gene*, 173 (2), 287–288 (1996).

Iwashita, K. et al. "Cloning and Sequencing of Beta–Glucosidase from *Aspergillus kawachii*", 1997 (Unpublished).

Barnett et al., "Cloning and Amplification of the Gene Encoding An Extracellular β–Glucosidase from *Trichoderma Reesei:* Evidence for Improved Rates of Saccharification of Cellulosic Substrates", *Bio/Technology* vol. 9, pp. 562–567, (1991).

Margolles–Clark et al., "Improved Production of *Trichoderma harzianum* Endochitinase by Expression in *Trichoderma ressei*", *Appl. Environ, Microbiol.*, 62(6): 2145–2151, (1996).

Joutsjouki et al., "Tranformation of *Trichodrma Ressel* with the *Hormoconics Resinae* Glucoamylase P (gamP) Gene: Production of a Heterologous Glucoamylase by *Trichoderma Ressel*, "*Curr. Genet.*,24:223–228, (1993).

Karhunen et al., "High Frequency One–Step Gene Replacement in *Trichoderma ressei* I. Endoglucanase 1 Overproduction", *Mol. Gen. Genet.*, 241:515–522, (1993).

Wakarchuck et al., "Mutational and Crystallographics Analyses of the Active–Site Residues of the Bacillus–Circulans Xylanase", *Protein Science*, 3:467–475, (1994).

Torronen et al., "The Two Major Xylanases from *Trichoderma reesei:* Characterization of Both Enzymes and Genes," *Bio/Technology*, 10:1461–1465, (1992).

Chen et al., "Nucleotide Sequence and Deduced Primary Structure of Cellobiohydrolase II from *Trichoderma Ressei*, "*Bio/Technology*, 5:274–278, (1987).

Gritz et al. "Plasmid–Encoded Hygromycin B Resistance: The Sequence of Hygromycin B Phosphotransferase Gene and Its Expression In *Escherichia coli*and *Saccharomyces Cerevisiae*,"*Gene*, 25:179–188, (1983).

Vanhanen et al., "Promoter Structure and Expression of the 3–Phosphoglycerate kinase–Encoding Gene (pgk1) of *Trichoderma reesei*", *Gene*, 106:129–133, (1991).

Lorito et al., "Biolistic Transformation of *Trichderma Harzianum* and *Gliocladium virens* Using Plasmid and Genomic DNA" *Curr. Genet.*, 24:349–356, (1993).

Goldman et al., "Transformation of *Trichoderma harzianum* By High–Voltage Electric Pulse", *Curr. Genet.*, 17:169–174, (1990).

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 72 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Trichoderma reesei (ix) FEATURE:
      (A) NAME/KEY: sig_peptide
      (B) LOCATION: 1..51
      (D) OTHER INFORMATION: /function= "cbh1 secretion signal"

(ix) FEATURE:
      (A) NAME/KEY: mat_peptide
      (B) LOCATION: 61..72
      (D) OTHER INFORMATION: /function= "mature beta-glucosidase"

(ix) FEATURE:
              (A) NAME/KEY: CDS
              (B) LOCATION: 1..72

(xi) SEQUENCE DESCRIPTION: SEQ ID NO:1:

```
ATG TAT CGG AAG TTG GCC GTC ATC TCG GCC TTC TTG GCC ACA GCT CGT        48
Met Tyr Arg Lys Leu Ala Val Ile Ser Ala Phe Leu Ala Thr Ala Arg
-20             -15                 -10                 -5

GCT CAG TCG GCA GTT GTA CCT CCT                                        72
Ala Gln Ser Ala Val Val Pro Pro
                  1
```

(2) INFORMATION FOR SEQ ID NO:2:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:2:

```
Met Tyr Arg Lys Leu Ala Val Ile Ser Ala Phe Leu Ala Thr Ala Arg
-20             -15                 -10                 -5

Ala Gln Ser Ala Val Val Pro Pro
                  1
```

(2) INFORMATION FOR SEQ ID NO:3:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
         (A) ORGANISM: Trichoderma reesei (ix) FEATURE:
         (A) NAME/KEY: sig_peptide
         (B) LOCATION: 1..99
         (D) OTHER INFORMATION: /function= "xln 2 signal peptide"

(ix) FEATURE:
         (A) NAME/KEY: mat_peptide
         (B) LOCATION: 109..120
         (D) OTHER INFORMATION: /function= "mature
             beta-glucosidase"

(ix) FEATURE:
         (A) NAME/KEY: CDS
         (B) LOCATION: 1..120

(xi) SEQUENCE DESCRIPTION: SEQ ID NO:3:

```
ATG GTC TCC TTC ACC TCC CTC CTC GCC GGC GTC GCC GCC ATC TCG GGC        48
Met Val Ser Phe Thr Ser Leu Leu Ala Gly Val Ala Ala Ile Ser Gly
-36 -35             -30                 -25

GTC TTG GCC GCT CCC GCC GCC GAG GTC GAA TCC GTG GCT GTG GAG AAG        96
Val Leu Ala Ala Pro Ala Ala Glu Val Glu Ser Val Ala Val Glu Lys
-20             -15                 -10                 -5

CGC CAG GCT AGA GTT GTA CCT CCT                                       120
Arg Gln Ala Arg Val Val Pro Pro
                  1
```

```
(2) INFORMATION FOR SEQ ID NO:4:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:4:

Met Val Ser Phe Thr Ser Leu Leu Ala Gly Val Ala Ala Ile Ser Gly
-36 -35             -30                 -25

Val Leu Ala Ala Pro Ala Ala Glu Val Glu Ser Val Ala Val Glu Lys
-20                 -15             -10                  -5

Arg Gln Ala Arg Val Val Pro Pro
```

GENETIC CONSTRUCTS AND GENETICALLY MODIFIED MICROBES FOR ENHANCED PRODUCTION OF BETA-GLUCOSIDASE

BACKGROUND OF THE INVENTION

1. Field of the Invention

This invention relates to genetic modification of microbes to enhance production of a commercially important enzyme, beta-glucosidase. This invention also relates to genetic constructs that dramatically increase the amount of beta-glucosidase produced by microbes containing these constructs.

2. Background of the Related Art

The possibility of producing ethanol from cellulose has received much attention due to the availability of large amounts of feedstock, the desirability of avoiding burning or land filling the materials, and the cleanliness of the ethanol fuel. The advantages of such a process for society are described in the cover story of the Atlantic Monthly, April 1996.

The natural cellulosic feedstocks for such a process are referred to as "biomass". Many types of biomass, including wood, agricultural residues, herbaceous crops, and municipal solid wastes, have been considered as feedstocks for ethanol production. These materials primarily consist of cellulose, hemicellulose, and lignin. This invention can be applied to the conversion of the cellulose to ethanol.

Cellulose is a polymer of the simple sugar glucose connected by beta 1,4 linkages. Cellulose is very resistant to degradation or depolymerization by acid, enzymes, or micro-organisms. Once the cellulose is converted to glucose, the resulting sugar is easily fermented to ethanol using yeast. The difficult challenge of the process is to convert the cellulose to glucose.

The oldest methods studied to convert cellulose to glucose are based on acid hydrolysis (review by Grethlein, "Chemical breakdown of Cellulosic Materials", J.Appl.Chem. Biotechnol. 28:296–308 (1978). This process can involve the use of concentrated or dilute acids. The concentrated acid process produces a high yield of glucose, but the recovery of the acid, the specialized materials of construction required, and the need to minimize water in the system are serious disadvantages of this process. The dilute acid process uses low levels of acid to overcome the need for chemical recovery. However, the maximum glucose yield is only about 55% of the cellulose, and a high degree of production of degradation products can inhibit the fermentation to ethanol by yeast. These problems have prevented the acid hydrolysis process from reaching commercialization.

To overcome the problems of the acid hydrolysis process, cellulose conversion processes have focused more recently on enzymatic hydrolysis, using cellulase enzymes. Enzymatic hydrolysis of cellulose is carried out by mixing the substrate and water to achieve a slurry of 5% to 12% cellulose and adding 5 to 50 International Units (IU) cellulase enzymes per gm cellulose. Typically, the hydrolysis is run for 12 to 150 hours at 35–60° C., pH 4–6.

Many microbes make enzymes that hydrolyze cellulose, including the wood rotting fungus Trichoderma, the compost bacteria Thermomonospora, Bacillus, and Cellulomonas; Streptomyces; and the fungi Humicola, Aspergillus and Fusarium. The enzymes made by these microbes are mixtures of proteins with three types of actions useful in the conversion of cellulose to glucose: endoglucanases (EG), cellobiohydrolases (CBH), and beta-glucosidase. EG and CBH enzymes are collectively referred to as "cellulose."

EG enzymes cut the cellulose polymer at random locations, opening it up to attack by CBH enzymes. As an example, Trichoderma strains produce at least four distinct EG enzymes, known as EGI, EGII, EGIII, and EGV.

CBH enzymes sequentially release molecules of cellobiose from the ends of the cellulose polymer. Cellobiose is the water-soluble beta-1,4-linked dimer of glucose. There are two primary CBH enzymes made by Trichoderma, CBHI and CBHII.

Beta-glucosidase enzymes hydrolyze cellobiose to glucose. Trichoderma makes one beta-glucosidase enzyme.

This final step in the cellulose hydrolysis which is catalyzed by beta-glucosidase is important, because glucose is readily fermented to ethanol by a variety of yeasts while cellobiose is not. Any cellobiose remaining at the end of the hydrolysis represents a loss of yield of ethanol. More importantly, cellobiose is an extremely potent inhibitor of the CBH and EG enzymes. Cellobiose decreases the rate of hydrolysis of the Trichoderma CBH and EG enzymes by 50% at a concentration of only 3.3 g/L. The decrease in rate of hydrolysis necessitates the addition of higher levels of cellulase enzymes, which adversely impacts the overall process economics. Therefore, the accumulation of cellobiose during hydrolysis is extremely undesirable for ethanol production.

Cellobiose accumulation has been a major problem in enzymatic hydrolysis because Trichoderma and the other cellulase-producing microbes make very little beta-glucosidase. Less than 1% of the total protein made by Trichoderma is beta-glucosidase. The low amount of beta-glucosidase results in a shortage of capacity to hydrolyze the cellobiose to glucose and an accumulation of 10 to 20 g/L of cellobiose during hydrolysis. This high level of cellobiose increases the amount of cellulase required by 10-fold over that if an adequate amount of beta-glucosidase were present.

Several approaches have been proposed to overcome the shortage of beta-glucosidase in cellulase enzymes.

One approach has been to produce beta-glucosidase using microbes that produce little cellulase, and add this beta-glucosidase exogenously to cellulase enzyme to enhance the hydrolysis. The most successful of such beta-glucosidase producing microbes have been *Aspergillus niger* and *Aspergillus phoenicis*. Beta-glucosidase from these microbes are available commercially as Novozym 188 from Novo Nordisk. However, the quantities required are much too costly for a commercial biomass to ethanol operation.

A second approach to overcoming the shortage of beta-glucosidase is to carry out cellulose hydrolysis simultaneously with fermentation of the glucose by yeast, the so-called simultaneous saccharification and fermentation (SSF) process. In an SSF system, the fermentation of the glucose removes it from solution. Glucose is a potent inhibitor of beta-glucosidase, so SSF is an attempt to increase the efficiency of beta-glucosidase. However, SSF systems are not yet commercially viable because the operating temperature for yeast of 28° C. is too low for the 50° C. conditions required by cellulase; operation at a compromise temperature of 37° C. is inefficient and prone to microbial contamination.

A third approach to overcoming the shortage of beta-glucosidase is to use genetic engineering to overexpress the enzyme and increase its production by Trichoderma. This approach was taken by Barnett, Berka, and Fowler, in "Cloning and Amplification of the Gene Encoding an Extracellular β-glucosidase from *Trichoderma reesei*: Evidence for Improved Rates of Saccharification of Cellulosic Substrates," Bio/Technology, Volume 9, June 1991, p. 562–567, herein referred to as "Barnett, et al."; and Fowler, Barnett, and Shoemaker in WO 92/10581, "Improved Saccharification of Cellulose by Cloning and Amplification of the β-glucosidase gene of *Trichoderma reesei*," herein referred to as "Fowler, et al."

Both Barnett, et al. and Fowler, et al. describe the insertion of multiple copies of the beta-glucosidase gene into *Trichoderma reesei* strain P40. Both groups constructed plasmid pSASβ-glu, a transformation vector containing the genomic *T. reesei* beta-glucosidase gene and the amdS selectable marker. The amdS gene is from *Aspergillus nidulans* and codes for the enzyme acetamidase, which allows transformed cells to grow on acetamide as a sole source of nitrogen. *T. reesei* does not contain a functional equivalent to the amdS gene and is therefore unable to utilize acetamide as a nitrogen source. The transformed cells contained 10 to 15 copies of the beta-glucosidase gene and produced 5.5- fold more beta-glucosidase than the untransformed cells.

The enhanced production of beta-glucosidase obtained by Barnett, et al. and Fowler, et al. is not sufficient to alleviate the shortage of beta-glucosidase for cellulose hydrolysis. The amount of beta-glucosidase made by natural Trichoderma strains, for example, must be increased at least 10-fold to meet the requirements of cellulose hydrolysis.

When overexpressing proteins in Trichoderma, one strategy is to link the gene of interest directly to the cbh1 promoter or to the cbh1 secretion signal. Since CBH1 is the most abundant protein produced by Trichoderma under cellulase-inducing conditions, the cbh1 promoter and secretion signal are thought to be very effective in directing the transcription and secretion of proteins encoded by a gene positioned after them in a genetic construct. Such a strategy has been successfully used to overexpress proteins from Trichoderma and other microorganisms (Margolles-Clark, Hayes, Harman and Penttila, 1996, "Improved Production of *Trichoderma harzianum* endochitinase by expression in *Trichoderma reesei*", Appl. Environ. Microbiol. 62(6): 2145–2151; Joutsjouki, Torkkeli and Nevalainen, 1993, "Transformation of *Trichoderma reesei* with the *Hormoconis resinae* glucoamylase P (gamP) gene: production of a heterologous glucoamylase by *Trichoderma reesei*", Curr. Genet. 24: 223–228; Karhunen, Mantyla, Nevalainen and Suominen, 1993,"High frequency one-step gene replacement in *Trichoderma reesei* 1. Endoglucanase I overproduction", Mol. Gen. Genet. 241: 515–522).

In spite of a significant amount of research effort, there has not been a means to produce sufficiently high levels of beta-glucosidase. Such a process would be a large step forward in the production of fuel alcohol from cellulose.

SUMMARY OF THE INVENTION

The inventors have made a discovery that enables the production of beta-glucosidase enzyme at levels far higher than currently achievable. The high levels of beta-glucosidase improve the efficiency of the enzymatic hydrolysis of cellulose to glucose. The resulting decrease in enzyme requirement, increased cellulose conversion, decrease in hydrolysis time, or a combination of these advantages, decreases the overall process costs of converting cellulose to ethanol.

The inventors have discovered genetic constructs that significantly increase the production of beta-glucosidase by recombinant microbes in which the constructs are expressed. The genetic constructs that accomplish this task comprise DNA sequences that encode a mature beta-glucosidase enzyme and a xylanase secretion signal.

As far as the inventors are aware, there have been no previous reports that linking the xylanase secretion signal to the mature beta-glucosidase enzyme increases the production of beta-glucosidase. In addition, the inventors are not aware of previous reports that linking the xylanase secretion signal to any non-xylanase mature protein increases the production of the protein. The inventors have discovered this surprising and unreported result. It was further surprising that the use of the xylanase secretion signal resulted in higher levels of beta-glucosidase than the use of the cbh1 secretion signal. Since xylanase comprises a much smaller proportion of the total protein produced by Trichoderma than does CBH1 (5% and 60%, respectively), one would expect that the cbh1 secretion signal would be more effective. The reasons why linking the xylanase secretion signal to the mature beta-glucosidase enzyme increases beta-glucosidase production are not known, but might relate to the similarity in length between the beta-glucosidase and xylanase secretion signals or to the lower abundance of xylanase against which the recombinant beta-glucosidase must compete for secretion out of the cell. However, the practice of the invention is not limited by these or any other specific reasons.

The present invention is not anticipated by Barnett, et al. and Fowler, et al., who each disclosed the enhanced expression of beta-glucosidase by recombinant means. The genetic construct of Barnett, et al. and Fowler, et al. comprises the beta-glucosidase promoter, coding region and secretion signal. The methods used by Barnett, et al. and Fowler, et al. are not as effective as the methods taught by the inventors, and do not anticipate the genetic constructs of the present invention.

In one aspect of our invention, a genetically modified microbe for producing beta-glucosidase comprises a beta-glucosidase construct not present in an untransformed microbe from which said genetically modified microbe is derived, said beta-glucosidase construct having a promoter, a xylanase secretion signal, and a mature beta-glucosidase coding region, wherein said genetically modified microbe is selected from the group consisting of Trichoderma, Humicola, Fusarium, Streptomyces, Thermomonospora, Bacillus, Cellulomonas, and Aspergillus, and wherein said genetically modified microbe produces at least about a 10-fold increase in production of beta-glucosidase relative to said untransformed microbe.

In another aspect, our invention includes a beta-glucosidase genetic construct comprising a promoter, a xylanase secretion signal, and a mature beta-glucosidase coding region, wherein said beta-glucosidase genetic construct, when introduced into and expressed in an untransformed microbial host selected from the group consisting of Trichoderma, Humicola, Fusarium, Streptomyces, Thermomonospora, Bacillus, Cellulomonas, and Aspergillus, produces at least about a 10-fold increase in production of beta-glucosidase relative to said untransformed microbial host.

In still another aspect of our invention, a genetically modified Trichoderma microbe for producing beta-glucosidase comprises a beta-glucosidase construct not present in an untransformed Trichoderma microbe, said beta-glucosidase construct having a promoter, a xylanase secretion signal, and a mature beta-glucosidase coding region, wherein said genetically modified Trichoderma produces at least about a 10-fold increase in production of beta-glucosidase relative to said untransformed Trichoderma microbe.

In yet another aspect, our invention includes a genetically modified *Trichoderma reesei* microbe for producing beta-glucosidase comprising a beta-glucosidase construct not present in an untransformed *Trichoderma reesei* microbe, said beta-glucosidase construct having a promoter, a xylanase secretion signal, and a mature beta-glucosidase coding region, wherein said genetically modified *Trichoderma reesei* microbe produces at least about a 10-fold increase in production of beta-glucosidase relative to said untransformed microbe.

In yet another aspect of our invention, a beta-glucosidase genetic construct comprises a promoter, a xylanase secretion signal, and a mature beta-glucosidase coding region, wherein said beta-glucosidase genetic construct, when introduced into and expressed in a Trichoderma microbe, produces at least about a 10-fold increase in production of beta-glucosidase relative to an untransformed Trichoderma microbe.

In still yet another aspect of our invention, a beta-glucosidase genetic construct comprises a promoter, a xylanase secretion signal, and a mature beta-glucosidase coding region, wherein said beta-glucosidase genetic construct, when introduced into and expressed in a *Trichoderma reesei* microbe, produces at least about a 10-fold increase in production of beta-glucosidase relative to an untransformed *Trichoderma reesei* microbe.

Other aspects of our invention will be better understood and advantages thereof more apparent in view of the following detailed description of the preferred embodiments and accompanying drawings.

DETAILED DESCRIPTION OF THE PREFERRED EMBODIMENTS

Figure 1:
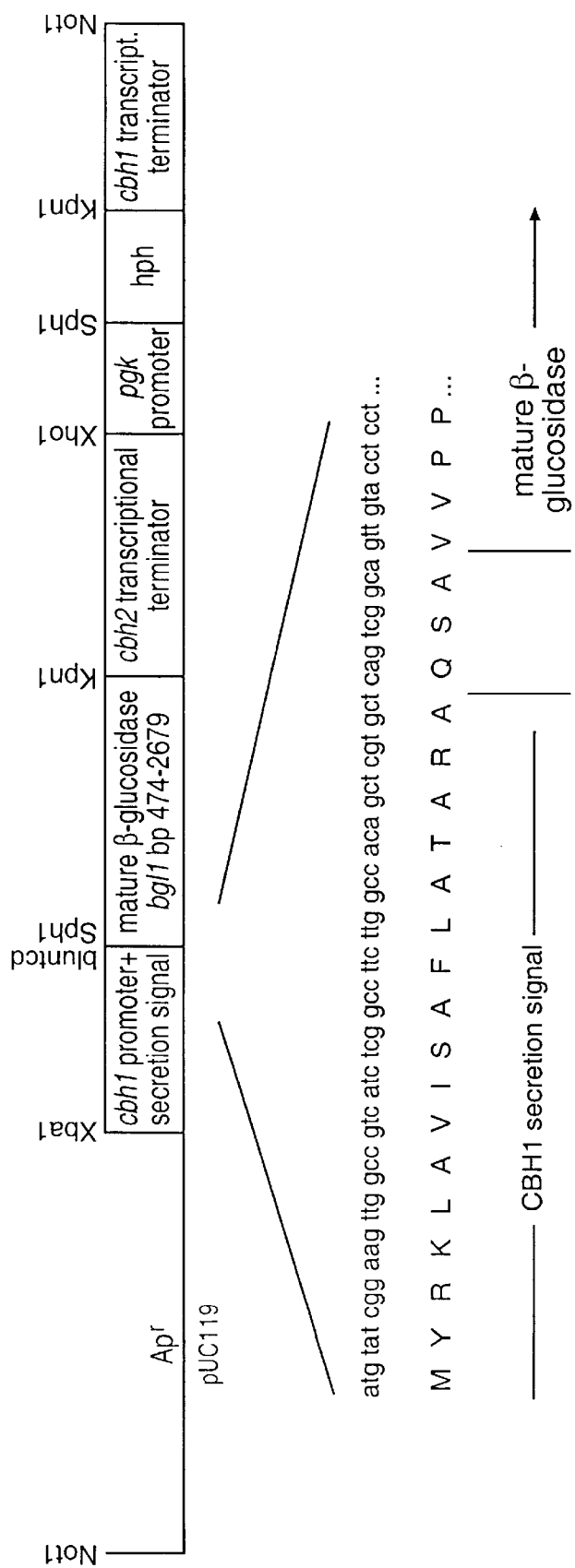
FIG. 1: Restriction map of the vector pCBG1-TV and the amino acid sequence of the CBH1 secretion signal/mature beta-glucosidase juncture (SEQ ID NO:1, SEQ ID NO:2).

Preferred embodiments of this invention are described by first defining the following terms.

Beta-glucosidase is an enzyme that hydrolyzes the glucose dimer cellobiose to glucose. There are many microbes that make beta-glucosidase, and the properties of these enzymes vary, including structure (molecular weight, three-dimensional orientation, amino acid composition, and active site) and catalytic activity (rate and kinetics of cellobiose hydrolysis, and ability to act on other substrates). However, in all cases beta-glucosidase enzyme can hydrolyze cellobiose to glucose. This may also be referred to as a mature beta-glucosidase enzyme when the active enzyme does not does not contain a beta-glucosidase secretion signal peptide.

The preferred beta-glucosidase for practicing the invention is the beta-glucosidase made by Trichoderma. This beta-glucosidase enzyme is of molecular weight 74,000 (as measured by SDS-polyacrylamide gel electrophoresis) and has an isoelectric point of 8.3 (as measured by non-denaturing isoelectric focusing polyacrylamide gel electrophoresis).

Beta-glucosidase gene is a region of DNA that codes for the production of beta-glucosidase enzyme. All microbes that produce beta-glucosidase possess at least one beta-glucosidase gene. A natural beta-glucosidase gene comprises a beta-glucosidase promoter, a secretion signal, a coding region and a transcriptional terminator. Microbes that do not produce beta-glucosidase do not generally contain an active or functional beta-glucosidase gene.

Beta-glucosidase secretion signal is the DNA sequence that encodes the beta-glucosidase secretion signal peptide.

Beta-glucosidase secretion signal peptide is the peptide sequence present at the amino terminus of the encoded beta-glucosidase enzyme that is subsequently removed during export of the mature beta-glucosidase enzyme out of the microbial cells. The secretion signal may comprise a pro-peptide, a pre-peptide or both.

Mature beta-glucosidase coding region comprises the DNA sequence necessary to encode the functional beta-glucosidase enzyme, as isolated from extracellular culture filtrates, but not the beta-glucosidase secretion signal.

Xylanase is an enzyme that hydrolyzes xylan to xylose. There are many microbes that make xylanase, and the properties of these enzymes vary, including structure (molecular weight, three-dimensional orientation, amino acid composition, and active site) and catalytic activity (rate and kinetics of xylan hydrolysis, and ability to act on other substrates). However, in all cases xylanase enzyme can hydrolyze xylan to xylose. This may also be referred to as a mature xylanase enzyme when the active enzyme does not contain a xylanase secretion signal peptide.

Some of the most important commercial xylanases are classified as Family 11 xylanases. A xylanase enzyme is classified in Family 11 if it possesses the amino acids common to Family 11, including two glutamic acid residues serving as the essential catalytic residues. These residues are amino acids 86 and 177 by *Trichoderma reesei* xylanase II numbering. The amino acids common to Family 11 xylanases are described in Wakarchuck, et al, Protein Science 3:467–475 (1994).

Xylanase gene is a region of DNA that codes for the production of xylanase enzyme. All microbes that produce xylanase possess at least one xylanase gene. A natural xylanase gene comprises a xylanase promoter, a secretion signal, a coding region and a transcriptional terminator. Microbes that do not produce xylanase do not generally contain an active or functional xylanase gene. Xylanase secretion signal is the DNA sequence that encodes the xylanase secretion signal peptide.

Xylanase secretion signal peptide is the peptide sequence present at the amino terminus of the encoded xylanase enzyme that is subsequently removed during export of the mature xylanase enzyme out of the microbial cells. The secretion signal may comprise a pro-peptide, a pre-peptide or both.

Cellulase is an enzyme that hydrolyzes cellulose to short beta 1,4-linked oligomers of glucose, including cellotetraose, cellotriose and cellobiose. There are many microbes that make one or more cellulase enzymes often classified as cellobiohydrolases or endoglucanases. The properties of these enzymes vary, including structure (molecular weight, three-dimensional orientation, amino acid composition, and active site) and catalytic activity (rate and kinetics of xylan hydrolysis, and ability to act on other substrates). However, in all cases cellulase enzymes can hydrolyze cellulose to short beta 1,4-linked oligomers of glucose, including cellotetraose, cellotriose and cellobiose.

Beta-glucosidase genetic construct refers to a gene comprising the elements necessary to produce beta-glucosidase. These include:

a. A mature beta-glucosidase coding region.

In a preferred embodiment, the mature beta-glucosidase coding region comprises a mature beta-glucosidase coding region of a Trichoderma gene. The DNA sequence of the mature beta-glucosidase coding region from *Trichoderma reesei* can be found in FIG. 1 of Barnett, et al.

Those skilled in the art are aware that a natural structural region can be modified by replacement, substitution, addition, or elimination of one or more nucleic acids without changing its function. The practice of the invention encompasses and is not constrained by such alterations to the mature beta-glucosidase coding region.

b. A xylanase secretion signal.

In a preferred embodiment, the xylanase secretion signal comprises a xylanase secretion signal of a Family 11 xylanase gene.

In a more preferred embodiment, the Family 11 xylanase gene is a Trichoderma xylanase gene.

In an even more preferred embodiment, the xylanase secretion signal comprises a xylanase secretion signal of *Trichoderma reesei* xylanase I (xln1) gene or xylanase II (xln2) gene. The DNA sequences of the *Trichoderma reesei* xlnI and xln2 secretion signals can be found in FIGS. 3 and 2, respectively, of Torronen, Mach, Messner, Gonzalez, Kalkkinen, Harkki and Kubicek, "The two major xylanases from *Trichoderma reesei:* characterization of both enzymes and genes," Bio/Technology 10: 1461–1465, 1992 (the gene identifications in the figure legends, as published, are reversed).

Those skilled in the art are aware that a natural secretion signal can be modified by replacement, substitution, addition, or elimination of one or more nucleic acids without changing its function. The practice of the invention encompasses and is not constrained by such alterations to the xylanase secretion signal.

c. Promoter

The practice of the invention is not constrained by the choice of promoter in the genetic construct. However, preferred promoters are the *Trichoderma reesei* cbh1, cbh2, egl, eg2, eg3, eg5, xln1 and xln2 promoters. The DNA sequence of the *Trichoderma reesei* cbh1 is deposited in GenBank under Accession Number D86235.

Figure 2:
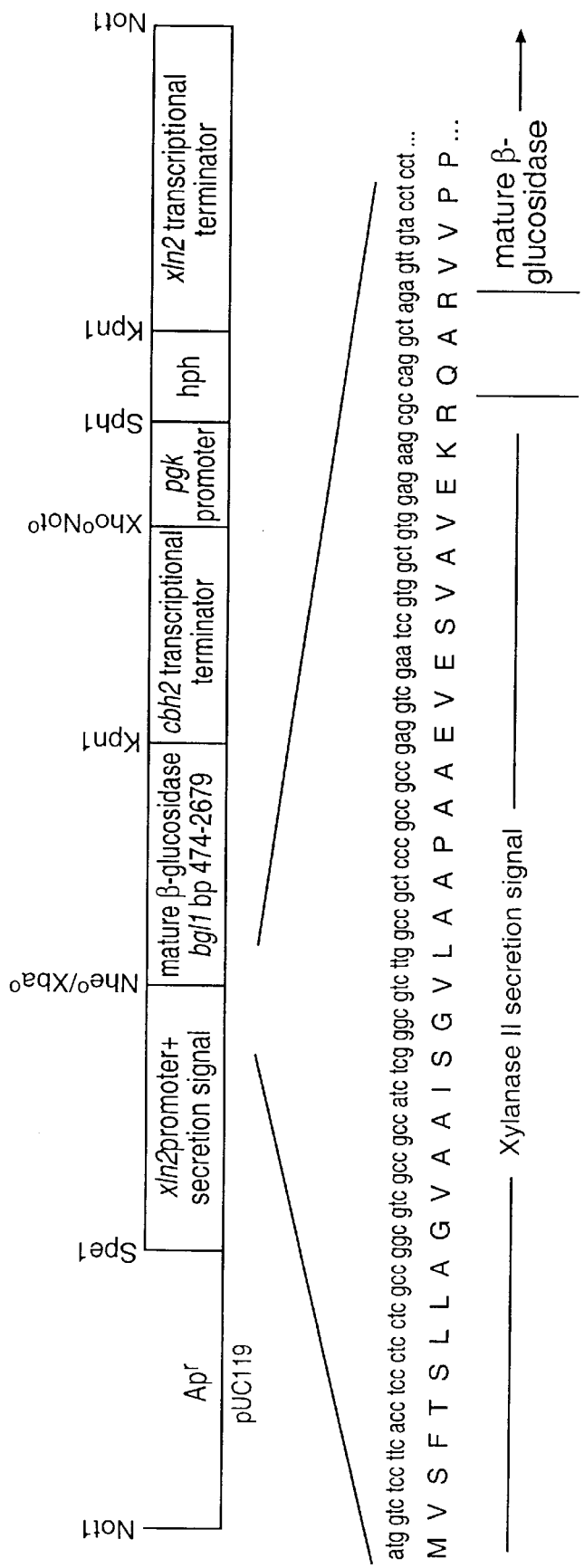
FIG. 2: Restriction map of the vector pXBG1-TV and the amino acid sequence of the xylanase II secretion signal/mature beta-glucosidase juncture (SEQ ID NO:3, SEQ ID NO:4).
Figure 3:
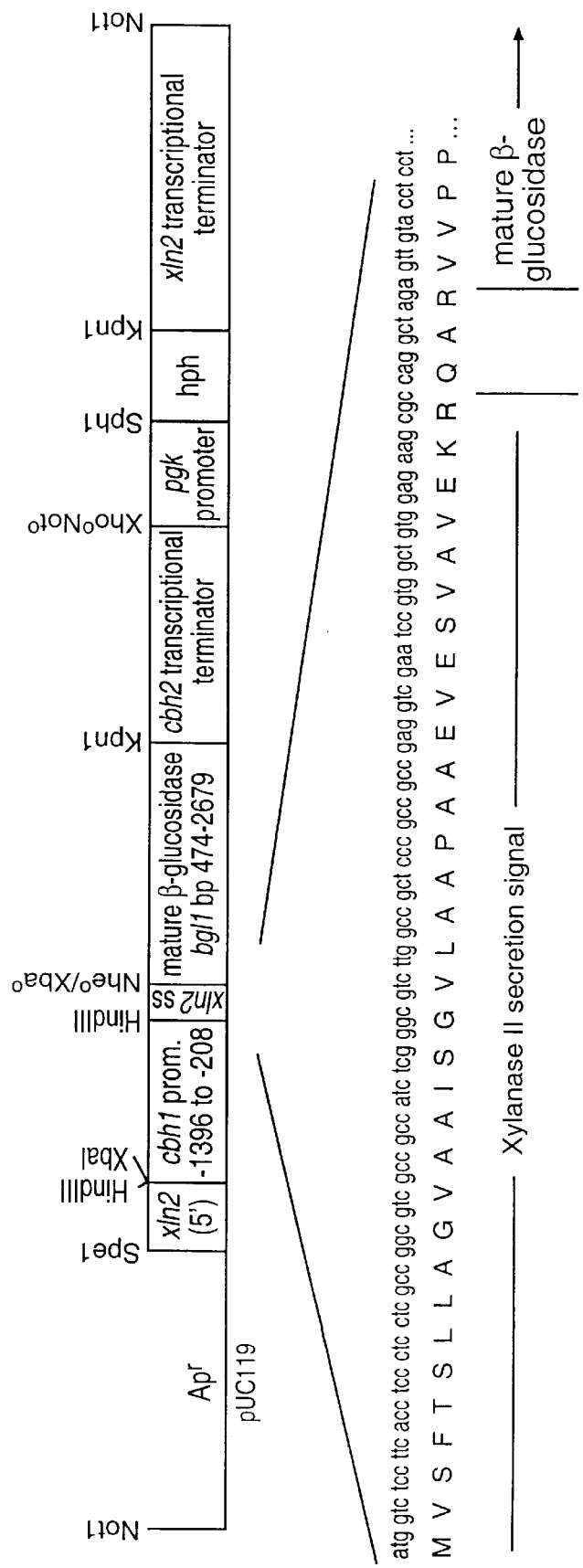
FIG. 3: Restriction map of the vector pC/XBG(Xba1)-TV and the amino acid sequence of the xylanase II secretion signal/mature beta-glucosidase juncture (SEQ ID NO:3, SEQ ID NO:4).

Those skilled in the art are aware that a natural promoter can be modified by replacement, substitution, addition or elimination of one or more nucleotides without changing its function. The practice of the invention encompasses and is not constrained by such alterations to the promoter.

d. Additional sequences between the xylanase secretion signal and the mature beta-glucosidase coding region The genetic constructs described in Examples 5, 6 and 7 contain nine additional base pairs of DNA sequence as shown in FIGS. 1–3; the first three encode the glutamine residue after the secretion signal of the *Trichoderma reesei* xylanase II gene, and the remaining six result from the insertion and/or modification of unique restriction sites used to join the xylanase secretion signal to the mature beta-glucosidase coding region. These DNA sequences result in the presence of additional amino acids between the xylanase secretion signal peptide and the mature beta-glucosidase enzyme. These DNA sequences, which may be natural or synthetic, may encode one or more of the amino acids of the mature xylanase protein corresponding to the xylanase secretion signal encoded by the construct or may result from the addition of restriction enzyme sites needed to join the xylanase secretion signal peptide and mature beta-glucosidase enzyme. The practice of the invention encompasses but is not constrained by the presence of additional DNA sequences between the xylanase secretion signal and the mature beta-glucosidase coding region.

e. other elements

The genetic construct contains a transcriptional terminator immediately downstream of the mature beta-glucosidase coding region. The practice of the invention is not constrained by choice of transcriptional terminator and may include as much DNA downstream (i.e., at the 3' end) of the stop codon of any known coding region as is sufficient to direct the termination of transcription by RNA polymerase. The transcriptional terminator present downstream of the mature beta-glucosidase coding region in the constructs described in Examples 5–7 comprises 1.9 kb of DNA 3' to the stop codon of the Trichoderma cbh2 gene.

The DNA sequence of the first 553 base pairs of the *Trichoderma reesei* cbh2 transcriptional terminator, which are located immediately downstream (or 3') of the TAA stop codon, can be found in FIG. 2 of Chen, Gritzali and Stafford, "Nucleotide Sequence and Deduced Primary Structure of Cellobiohydrolase II from *Trichoderma reesei*," Bio/Technology 5: 274–278, 1987.

The genetic construct contains a selectable marker which may be present upstream or downstream of the genetic construct (i.e., at the 5' or 3' end of the construct) on the same plasmid vector or may be cotransformed with the construct on a separate plasmid vector. Choices of selectable markers are well known to those skilled in the art and include genes (synthetic or natural) that confer to the transformed cells the ability to utilize a metabolite that is not normally metabolized by the microbe (e.g., the *A. nidulans* amdS gene encoding acetamidase and conferring the ability to grow on acetamide as the sole nitrogen source) or antibiotic resistance (e.g., the *Escherichia coli* hph gene encoding hygromycin-b-phosphotransferase and conferring resistance to hygromycin). If the host strain lacks a functional gene for the marker chosen, then that gene may be used as a marker. Examples of such markers include trp, pyr4, pyrG, argB, leu, and the like. The corresponding host strain would therefore have to lack a functional gene corresponding to the marker chosen, i.e., trp, pyr, arg, leu and the like. The selectable marker used in the genetic constructs described in Examples 5–7 is the *E. coli* hph gene expressed from the Trichoderma phosphoglycerate kinase (pgk) promoter.

Figure 4:
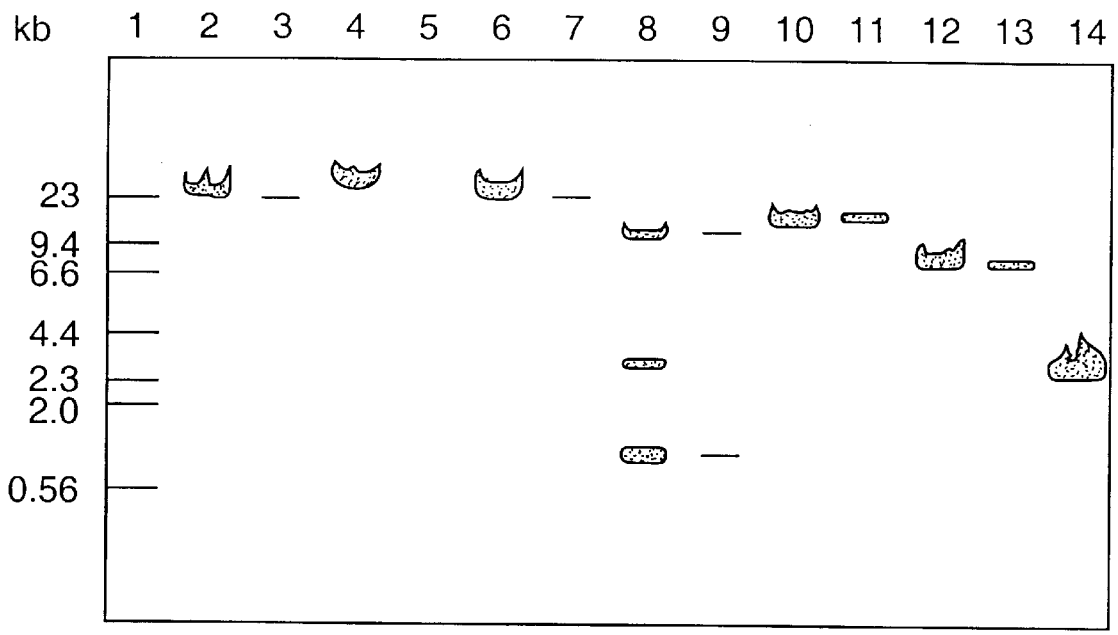
FIG. 4: Southern blot of genomic DNA isolated from *T. reesei* strains RutC30 and M2C38 and probed with a labeled DNA fragment comprising the M2C38 xylanase promoter plus secretion signal.

The DNA sequence of the *E. coli* hph gene can be found in FIG. 4 of Gritz and Davies, "Plasmid-encoded hygromycin B resistance: the sequence of hygromycin B phosphotransferase gene and its expression in *Escherichia coli* and *Saccharomyces cerevisiae*," Gene 25: 179–188, 1983; the DNA sequence of the *Trichoderma reesei* pgk promoter can be found in FIG. 2 of Vanhanen, Saloheimo, Ilmen, Knowles and Penttila, "Promoter structure and expression of the 3-phosphoglycerate kinase-encoding gene (pgk1) of *Trichoderma reesei*," Gene 106: 129–133, 1991.

One preferred embodiment of the invention comprises the beta-glucosidase genetic construct described thus far. The practice of our invention is not constrained by the method of making the construct, which can include, but is not restricted to, standard molecular biology techniques such as isolation of plasmid DNA from *E. coli* by alkaline lysis, digestion of plasmid DNA with restriction endonucleases, separation and isolation of DNA fragments by agarose gel electrophoresis, ligation of DNA fragments with T4 DNA ligase, insertion of unique restriction sites at the ends of DNA fragments by polymerase chain reaction or the addition of oligonucleotide linkers, and the blunting of DNA fragments with T4 DNA polymerase or Klenow fragment of *E. coli* DNA polymerase I.

Examples 1–7 describe procedures for making such genetic constructs.

In another preferred embodiment of our invention, the beta-glucosidase genetic construct is introduced into and expressed in a microbial host to create a genetically modified microbe. The resulting genetically modified microbe produces an increased level of beta-glucosidase relative to the untransformed microbial host. The genetically modified microbe produces an increased level of beta-glucosidase of preferably at least about 10-fold relative to the untransformed microbial host, more preferably at least about 40-fold relative to the untransformed microbial host, and most preferably at least about 120-fold relative to the untransformed microbial host.

This invention encompasses any method of introducing the beta-glucosidase genetic construct into the microbial host familiar to those skilled in the art, including but not limited to, calcium chloride treatment of bacterial cells or fungal protoplasts to weaken the cell membranes, addition of polyethylene glycol to allow for fusion of cell membranes, depolarization of cell membranes by electroporation, or shooting the DNA through the cell wall and membranes via microprojectile bombardment with a particle gun.

Example 8 describes the procedures for introducing the beta-glucosidase genetic construct into Trichoderma spores using a particle gun.

A 10-fold enhancement of beta-glucosidase production relative to the untransformed microbial host reflects a significant enhancement that is well above the natural variability of the strain and commercially significant. The degree of enhancement of beta-glucosidase by this method has been as high as 126-fold and could reach over 1000-fold. The measurement of the degree of enhancement of beta-glucosidase production is by growth of the culture and measurement of the beta-glucosidase activity, as described in Example 11. It is believed that genetic constructs of our invention will produce any level of enhancement greater than about 10-fold.

It is understood by those skilled in the art that the specific beta-glucosidase activity of an enzyme mixture (in IU/mg protein) can be increased by decreasing the amount of cellulase and other proteins in the enzyme mixture. This can be done by physical and mechanical separations of the enzyme mixture or by deletion of the cellulase or other genes by recombinant means. Such methods have little or no effect on the actual production of beta-glucosidase by the microorganism. These procedures may, however, be optionally included in the practice of our invention.

In a preferred embodiment, the microbial host is a member of the species of Trichoderma, Humicola, Fusarium, Aspergillus, Streptomyces, Thermomonospora, Bacillus, or Cellulomonas. These species are well suited because they produce cellulase in addition to beta-glucosidase. In addition, methods have been published for the introduction of DNA constructs into cellulase-producing strains of Trichoderma (Lorito, Hayes, DiPietro and Harman, 1993, "Biolistic Transformation of *Trichoderma harzianum* and *Gliocladium virens* using plasmid and genomic DNA," Curr. Genet. 24: 349–356; Goldman, VanMontagu and Herrera-Estrella, 1990, "Transformation of *Trichoderma harzianum* by high-voltage electric pulse", Curr. Genet. 17:169–174; Penttila, Nevalainen, Ratto, Salminen and Knowles, 1987, "A versatile transformation system for the cellulolytic fungus *Trichoderma reesei*", Gene 6: 155–164), Aspergillus (Yelton, Hamer and Timberlake, 1984, "Transformation of *Aspergillus nidulans* using a trpC plasmid," Proc. Natl. Acad. Sci. USA 81: 1470–1474), Fusarium (Bajar, Podila and Kolattukudy, 1991, "Identification of a fungal cutinase promoter that is inducible by a plant signal via a phosphorylated transacting factor," Proc. Natl. Acad. Sci. USA 88: 8202–8212), Streptomyces (Hopwood et al., 1985, "Genetic Manipulation of Streptomyces: a laboratory manual," The John Innes Foundation, Norwich, UK) and Bacillus (Brigidi, DeRossi, Bertarini, Riccardi and Matteuzzi, 1990, "Genetic transformation of intact cells of *Bacillus subtilis* by electroporation," FEMS Microbiol. Lett. 55: 135–138).

The genetic constructs used in these published transformation methods are similar to those described in Examples 5–7 in that they contain a promoter linked to a protein coding region (which may encode a selectable marker) and a transcriptional terminator. In most cases, the genetic constructs are linked to a selectable marker gene.

Although there are no published methods for the transformation of Humicola, Thermomonospora or Cellulomonas, it is believed that the transformation methods for other filamentous fungi or bacteria can be optimized for Humicola, Thermomonospora or Cellulomonas strains by virtue of the similar morphologies and physiologies of these species to those for which transformation methods have been published. In addition, transformation methods such as electroporation and particle bombardment have been used to introduce DNA into many different cell types including mammalian and plant cells, bacterial, yeast, and fungal cells.

In a preferred embodiment, the xylanase secretion signal is native to the microbial host from which said genetically modified microbe is derived (i.e., the source of the xylanase secretion signal is the same type of microbial host as the microbial host from which said genetically modified microbe is derived).

In a more preferred embodiment, the microbial host is Trichoderma.

In a more preferred embodiment, the microbial host is *Trichoderma reesei*.

EXAMPLES

Example 1 describes the isolation of genomic DNA from *Trichoderma reesei* strains RutC30, M2C38, BTR48 and the genetically modified derivatives of these strains. Examples 2–7 describe the construction of genomic DNA libraries, the cloning of various genes, and several genetic constructs from *Trichoderma reesei* strain M2C38. Examples 9 and 11–15 describe the transformation and expression of beta-glucosidase genetic constructs in *Trichoderma reesei* strains M2C38, BTR48, and RutC3X.

*Trichoderma reesei* strains M2C38 and BTR48 are proprietary strains of Iogen Corporation, and were derived from *Trichoderma reesei* RutC30 (ATCC 56765, Montenecourt and Eveleigh, 1979, "Selective isolation of high yielding cellulase mutants of *T. reesei*", Adv. Chem. Ser. 181:

289–301), which was in turn derived from *Trichoderma reesei* Qm6A (ATCC 13631 Mandels and Reese, 1957 "Induction of cellulase in *Trichoderma viride* as influenced by carbon sources and metals", J. Bacteriol. 73: 269–278).

In Example 1 and subsequent Examples, restriction endonucleases, T4 DNA polymerase, T4 DNA ligase and Klenow fragment of *E. coli* DNA polymerase 1 were purchased from Gibco/BRL, New England Biolabs, Boehringer Mannheim or Pharmacia and used as recommended by the manufacturer. Pwo polymerase with proof-reading activity (Boehringer Mannheim) was used in all polymerase-chain reactions (PCR) according to the manufacturer's protocol. Hygromycin B was purchased from CalBiochem.

EXAMPLE 1

Isolation of *Trichoderma reesei* Genomic DNA

To isolate genomic DNA, 50 ml of Potato Dextrose Broth (Difco) was inoculated with *T. reesei* spores collected from a Potato Dextrose Agar plate with a sterile inoculation loop. The cultures were shaken at 200 rpm for 2–3 days at 28° C. The mycelia was filtered onto a sterile GFA glass microfibre filter (Whatman) and washed with cold, deionized water. The fungal cakes were frozen in liquid nitrogen and crushed into a powder with a pre-chilled mortar and pestle; 0.5 g of powdered biomass were resuspended in 5 ml of 100 mM Tris, 50 mM EDTA, pH 7.5 plus 1% sodium dodecyl sulphate (SDS). The lysate was centrifuged (5000 g for 20 min, 4° C.) to pellet cell debris. The supernatant was extracted with 1 volume buffer (10 mM Tris, 1 mM EDTA, pH 8.0) saturated phenol followed by extraction with 1 volume of buffer-saturated phenol:chloroform:isoamyl alcohol (25:24:1) in order to remove soluble proteins. DNA was precipitated from the solution by adding 0.1 volume of 3M sodium acetate, pH 5.2 and 2.5 volumes of cold 95% ethanol. After incubating for at least 1 h at −20° C., the DNA was pelleted by centrifugation (5000 g for 20 min, 4° C.), rinsed with 10 ml 70% ethanol, air-dried and resuspended in 1 ml 10 mM Tris, 1 mM EDTA, pH8.0. RNA is digested by the addition of Ribonuclease A (Boehringer Mannheim) added to a final concentration of 0.1 mg/ml and incubation at 37° C. for 1 hour. Sequential extractions with 1 volume of buffer-saturated phenol and 1 volume of buffer-saturated phenol:chloroform:isoamyl alcohol (25:24:1) are used to remove the ribonuclease from the DNA solution. The DNA is again precipitated with 0.1 volume of 3M sodium acetate, pH 5.2 and 2.5 volumes of cold 95% ethanol, pelleted by centrifugation, rinsed with 70% ethanol, air-dried and resuspended in 50 μl of 10 mM Tris, 1 mM EDTA, pH 8.0. The concentration of DNA was determined by measuring the absorbance of the solution at 260 nm (p. C1 in Sambrook, Fritsch and Maniatis, "Molecular Cloning: A Laboratory Manual, Second Edition", Cold Spring Harbor Press 1989, hereafter referred to as Sambrook et al.).

EXAMPLE 2

Construction of *T. reesei* Genomic Libraries

Two plasmid libraries and one phage library were constructed using genomic DNA isolated from *T. reesei* strain M2C38. The plasmid libraries were constructed in the vector pUC119 (Viera and Messing, "Isolation of single-stranded plasmid DNA", Methods Enzymol. 153:3, 1987) as follows: 10 μg genomic DNA was digested for 20 hrs at 37° C. in a 100 μl volume with 2 units/μg of HindIII, BamHI or EcoRI restriction enzymes. The digested DNA was fractionated on a 0.75% agarose gel run in 0.04M Tris-acetate, 1 mM EDTA, and stained with ethidium bromide. Gel slices corresponding to the sizes of the genes of interest (based on published information and Southern blots) were excised and subjected to electro-elution to recover the DNA fragments (Sambrook et al., pp. 6.28–6.29). These enriched fractions of DNA were ligated into pUC119 in order to create gene libraries in ligation reactions containing 20–50 μg/ml DNA in a 2:1 molar ratio of vector:insert DNA, 1 mM ATP and 5 units T4 DNA ligase in a total volume of 10–15 μl at 4° C. for 16 h. *Escherichia coli* strain HB101 was electroporated with the ligation reactions using the Cell Porator System (Gibco/BRL) following the manufacturer's protocol and transformants selected on LB agar containing 70 μg/ml amplicillin.

The phage library was constructed in the lambda vector lambda DASH (Stratagene, Inc.) as follows: genomic DNA (3 μg) was digested with 2, 1, 0.5 and 0.2 units/μg Bam HI for 1 hour at 37° C. to generate fragments 9–23 kB in size. The DNA from each digest was purified by extraction with 1 volume Tris-saturated phenol:choroform:isoamyl alcohol (25:24:1) followed by precipitation with 10 μl 3M sodium acetate, pH 5.2 and 250 μl 95% ethanol (−20° C.). The digested DNA was pelleted by microcentrifugation, rinsed with 0.5 ml cold 70% ethanol, air-dried and resuspended in 10 μl sterile, deionized water. Enrichment of DNA fragments 9–23 kB in size was confirmed by agarose gel electrophoresis (0.8% agarose in 0.04 M Tris-acetate, 1 mM EDTA). Digested DNA (0.4 μg) was ligated to 1 μg lambdaDASH arms predigested with BamHI (Stratagene) in a reaction containing 2 units T4 DNA ligase and 1 mM ATP in a total volume of 5 μl at 4° C. overnight. The ligation mix was packaged into phage particles using the GigaPack® II Gold packaging extracts (Stratagene) following the manufacturer's protocol. The library was titered using the *E. coli* host strain XL1-Blue MRA (P2) and found to contain $3 \times 10^5$ independent clones.

EXAMPLE 3

Isolation of *T. reesei* M2C38 Clones of the Cellobiohydrolase I (cbh1), Cellobiohydrolase II (cbh2) and β-glucosidase (bgl1) Genes from the pUC119 Libraries

*E. coli* HB101 transformants harboring cbh1, cbh2 or bgl1 clones from the recombinant pUC119-Hind III, -BamHIor -EcoRIlibraries were identified by colony lift hybridization: $1-3 \times 10^4$ colonies were transferred onto HyBond™ nylon membranes (Amersham); membranes were placed colony-side up onto blotting paper (VWR 238) saturated with 0.5 M NaOH, 1 M NaCl for 5 min to lyse the bacterial cells and denature the DNA; the membranes were then neutralized by placing them colony-side up onto blotting paper (VWR 238) saturated with 1.5 M Tris, pH 7.5 plus 1 M NaCl for 5 min; the membranes were allowed to air-dry for 30 min and the DNA was then fixed to the membranes by baking at 80° C. for 2 h.

$^{32}$P-labelled probes were prepared by PCR amplification of short (0.7–1.5 kB) fragments of the bgl1, cbh1 and cbh2 coding regions from the enriched pool of Hind III, BamHI or EcoRI fragments, respectively, in a labeling reaction containing 10–50 ng target DNA, 0.2 mM each d(GCT)TP, 0.5 μM dATP, 20-40 μCi alpha-$^{32}$P-dATP, 10 pmole oligonucleotide primers and 0.5 units Taq polymerase in a total volume of 20 μl. The reaction was subjected to 6–7 cycles of amplification (95° C., 2 min; 56° C., 1.5 min; 70° C., 5 min). The amplified, 32P-labelled DNA was precipitated by the addition of 0.5 ml 10% (w/v) trichloroacetic acid and 0.5 mg yeast tRNA. The DNA was pelleted by microcentrifugation, washed twice with 1 ml 70% ethanol, air-dried and resuspended in 1M Tris pH7.5, 1 mM EDTA.

Nylon membranes onto which the recombinant pUC119 plasmids had been fixed were prehybridized in heat-sealed bags for 1 h at 60–65° C. in 1 M NaCl, 1% SDS, 50 mM Tris, 1 mM EDTA pH 7.5 with 100 µg/ml denatured sheared salmon sperm DNA. Hybridizations were performed in heat-sealed bags in the same buffer with only 50 µg/ml denatured sheared salmon sperm DNA and $5\times10^6$–$5\times10^7$ cpm of denatured bgl1, cbh1 or cbh2 probe for 16–20 h at 60–65° C. Membranes were washed once for 15 min with 1 M NaCl, 0.5% SDS at 60° C., twice for 15 min each with 0.3M NaCl, 0.5% SDS at 60° C. and once for 15 min with 0.03M NaCl, 0.5% SDS at 55° C. Membranes were again placed in heat-sealed bags and exposed to Kodak RF X-ray film to 16–48 h at −70° C. The X-ray film was developed following the manufacturer's protocols. Colonies giving strong or weak signals were picked and cultured in 2' YT media supplemented with 70 µg/ml ampicillin. Plasmid DNA was isolated from these cultures using the alkaline lysis method (Sambrook et al., pp. 1.25–1.28) and analyzed by restriction digest, Southern hybridization (Sambrook et al., pp. 9.38–9.44) and PCR analysis (Sambrook et al., pp. 14.18–14.19).

Clones carrying the bgl1 gene were identified by colony lift hybridization of the pUC119-Hind III library (Example 2) with a 1.0 kb bgl1 probe prepared using oligonucleotide primers designed to amplify bp 462–1403 of the published bgl1 sequence (Barnett et al.). A bgl1 clone, pJEN200, was isolated containing a 6.0 kb Hind III fragment corresponding to the promoter, structural gene and termination sequences. Clones carrying the cbh1 gene were identified by colony lift hybridization of the pUC119-BamHI library with a 0.7 kb cbh1 probe prepared using oligonucleotide primers designed to amplify bp 597–1361 of the published cbh1 sequence (Shoemaker, Schweikart, Ladner, helfand, Kwok, Myambo and Innis, "Molecular cloning of exo-cellobiohydrolase 1 derived from *Trichoderma reesei* strain L27", Bio/Technology 1: 691–696, 1983 hereafter referred to as Shoemaker et al.). A cbh1 clone, pCOR132, was isolated containing a 5.7 kb BamHI fragment corresponding to the promoter (4.7 kb) and 1 kb of the cbh1 structural gene. From this, a 2.5 kb EcoRI fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoRI library with a 1.5 kb cbh2 probe prepared using oligonucleotide primers designed to amplify bp 580–2114 of the published cbh2 sequence (Chen, Gritzali and Stafford, "Nucleotide sequence and deduced primary structure of cellobiohydrolase II from *Trichoderma reesei*", Bio/Technology 5: 274–278, 1987, hereafter referred to as Chen et al.). A cbh2 clone, pZUK600, was isolated containing a 4.8 kb EcoRI fragment corresponding to the promoter (600 bp), structural gene (2.3 kb) and terminator (1.9 kbp).

EXAMPLE 4

Cloning of *T. reesei* M2C38 cbh1 Terminator, Xylanase II (xln2) Gene, Phosphoglycerate Kinase Promoter (pgk p)

Digoxigen-11-dUTP labelled probes were prepared from PCR amplified coding regions of the cbh1, xln2 and pgk genes by random prime labeling using the DIG Labeling and Detection kit (Boehringer Mannheim) and following the manufacturer's protocols. Genomic clones containing the cbh1, xln2 and pgk genes were identified by plaque-lift hybridization of the lambdaDASH library. For each gene of interest, $1\times10^4$ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 min; the membranes were then neutralized by placing them plaque-side up onto blotting paper (VWR238) saturated with 1.5 M Tris, pH 7.5 plus 1 M NaCl for 5 min; the membranes were allowed to air-dry for 30 min and the DNA was then fixed to the membranes by baking at 80° C. for 2 h. The membranes were prehybridized in heat-sealed bags in a solution of 6× SSPE, 5× Denhardt's, 1% SDS plus 100 µg/ml denatured, sheared salmon sperm DNA at 65° C. for 2 h. The membranes were then hybrized in heat-sealed bags in the same solution containing 50 µg/ml denatured, sheared salmon sperm DNA and 0.5 µg of digoxigen-dUTP labelled probes at 65° C. overnight. The membranes were washed twice for 15 min in 2× SSPE, 0.1% SDS at RT, twice for 15 min in 0.2× SSPE, 0.1% SDS at 65° C. and once for 5 min in 2× SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Boehringer Mannheim) following the manufacturer's protocol. Positively hybridizing clones were purified further by a second round of screening with the digoxigen-dUTP labeled probes. Individual clones were isolated and the phage DNA purified as described in Sambrook, et al. (1989) pp. 2.118–2.121 with the exception that the CsCl gradient step was replaced by extraction with 1 volume of phenol:choroform:isoamyl alcohol (25:24:1) and 1 volume of chloroform:isoamyl alcohol (24:1). The DNA was precipitated with 0.1 volume of 3M sodium acetate, and pH 5.2 and 2.5 volumes cold 95% ethanol. The precipitated phage DNA was washed with 0.5 ml cold 70% ethanol, air-dried and resuspended in 50 µl 10 mM Tris, 1 mM EDTA pH8.0. Restriction fragments containing the genes of interest were identified by restriction digests of the purified phage DNA and Southern blot hybridization (Sambrook et al., pp. 9.38–9.44) using the same digoxigen-dUTP labeled probes used to screen the lambdaDASH library. The membranes were hybridized and positively hybridizing fragments visualized by the same methods used for the plaque lifts. Once the desired restriction fragments from each lambda DASH clone were identified, the restriction digests were repeated, the fragments were resolved on a 0.8% agarose gel in TAE and the desired bands excised. The DNA was eluted from the gel slices using the Sephaglas BandPrep Kit (Pharmacia) following the manufacturer's protocol.

Clones carrying the cbh1 gene were identified by colony lift hybridization of the lambdaDASH library (example 2) with a cbh1 probe comprising bp 45–2220 of the published cbh1 sequence (Shoemaker et al.). A 1.8 kb BamHI fragment containing the 3' end of the cbh1 coding region (0.5 kb) and the cbh1 terminator (1.3 kb) was isolated by restriction digestion of phage DNA purified from a lambdaDASH cbh1 clone. This fragment was subcloned into the BamHI site of the *E.coli* plasmid vector pUC119 to generate the plasmid pCB1Ta. Clones carrying the xln2 gene were identified by colony lift hybridization of the lambdaDASH library (example 2) with a xln2 probe comprising bp 100–783 of the published xln2 sequence (Saarelainen, Paloheimo, Fagerstrom, Suominen and Nevalainen, "Cloning, sequencing and enhanced expression of the *Trichoderma reesei* endoxylanase II (pI 9) gene xln2", Mol. Gen. Genet. 241:

497–503, 1993, hereafter referred to as Saarelainen et al.). A 5.7 kb KpnI fragment containing the promoter (2.3 kb), coding region (0.8 kb) and terminator (2.6 kb) the xln2 gene was isolated by restriction digestion of phage DNA purified from a lambdaDASH xln2 clone. This fragment was subcloned into the KpnI site of pUC119 to generate the plasmid pXYN2K-2. Clones carrying the pgk gene were identified by colony lift hybridization of the lambdaDASH library (Example 2) with a pgk1 probe comprising bp 4–1586 of the published pgk sequence (Vanhanen, Penttila, Lehtovaara and Knowles, "Isolation and characterization of the 3-phosphoglycerate kinase gene (pgk) from the filamentous fungus *Trichoderma reesei*", Curr. Genet. 15: 181–186, 1989). A 5.0 kb EcoRI fragment containing the promoter (2.9 kb), coding region (1.6 kb) and terminator (0.5 kb) of the pgk gene was isolated by restriction digestion of phage DNA purified from a lambdaDASH pgk clone. This fragment was subcloned into the EcoRI site of pUC119 to generate the plasmid pGK5.0.

EXAMPLE 5

Construction of β-glucosidase Overexpression Vector pCBG1-TV

This Example describes the construction of a vector containing the Trichoderma cellobiohydrolase I promoter and secretion signal and the mature beta-glucosidase coding region.

A DNA fragment containing the bgl1 coding region minus the β-glucosidase secretion signal (bp 474–2679) was amplified by PCR from the pJEN200 template using primers homologous to the published bgl1 sequence containing either an SphI site 5' to Val32 of the encoded β-glucosidase or a KpnI site 3' to the bgl1 stop codon using Pwo polymerase. This amplified fragment was digested with SphI and KpnI and inserted into pCB219N digested with SphI and KpnI to generate pBgstrf. To make pCB219N, a cbh2 terminator fragment was amplified from the pZUK600 template using a primer homologous to bp 2226–2242 of the published 3' untranslated region of the cbh2 gene (Chen et al., 1987) containing a KpnI site at the 5' end and the pUC forward primer (Cat. No. 1224, New England Biolabs) which anneals downstream of the EcoRI site at the 3' end of cbh2 in pZUK600. This fragment was digested at the engineered KpnI and EcoRI sites and inserted into the corresponding sites of pUC119 to generate pCB219. An EcoRI-NotI adaptor (Cat. No. 35310-010, Gibco/BRL) was inserted into the unique EcoRI site of pCB219 to generate pCB219N. A fragment containing the cbh1 promoter and secretion signal was amplified from pCB152 using a cbh1 specific primer (bp 249–284 of the published cbh1 sequence, Shoemaker et al., 1983) containing a SphI site 3' to Ser19 of the encoded CBH1 and pUC forward primer (Cat. No. 1224, New England Biolabs) which anneals upstream of the EcoRI site at the 5' end of cbh1 in pCB152. The cbh1 promoter+ secretion signal PCR product was digested with SphI and EcoRI and inserted into the corresponding sites in pBR322L (a derivative of pBR322 in which the region between the SphI and SalI sites was replaced with an SphI-NotI-SalI linker) to generate pBR322LCS. To make the expression cassette, the bgl1 coding region and cbh2 terminator were isolated from pBgstrf as a 4.1 kb SphI/NotI fragment and inserted into pBR322LCS digested with SphI and NotI. In order to maintain the correct reading frame at the juncture of the cbh1 secretion signal and the mature β-glucosidase, the resultant plasmid, pCBGstrf, was linearized at the unique SphI site and the SphI site was blunted with T4 DNA polymerase. The resulting plasmid, pCBG1, was then further modified by conversion of the unique NotI site at the 3' end of the cbh2 terminator to a unique XhoI site by the addition of XhoI linkers (Cat. No. 1073, New England Biolabs). The final plasmid, pCBG1-Xho, is the expression cassette plasmid.

The *E.coli* hygromycin phosphotransferase gene (hph) used as a selectable marker for *T. reesei* was amplified with Pwo polymerase from the plasmid pVU1005 (Van den Elzen, Townsend, Lee and Bedbrook, "A chimaeric hygromycin resistance gene as a selectable marker in plant cells", Plant Mol. Biol. 5: 299–302, 1989). The primers were designed to introduce SphI and KpnI sites at the 5' and 3' ends of the hph coding region (bp 211–1236 of the published hph sequence, Gritz and Davies, "Plasmid-encoded hygromycin b resistance: the sequence of hygromycin B phosphotransferase gene and its expression in *Escherichia coli* and *Saccharomyces cerevisiae*" Gene 25: 179–188,1983), respectively. The PCR product was digested with SphI and KpnI and inserted into the corresponding sites in the polylinker region of pUC119. The resulting plasmid, pHPT100 was used as the starting plasmid for the construction of the selection cassette. Two new linker regions were introduced into this plasmid to facilitate the cloning of the promoter and terminator fragments. A HindIII-XbaI-XhoI-SphI linker was inserted between the HindIII and SphI sites as well as a KpnI-NotI-SacI linker which was inserted between the KpnI and SacI sites of pUC119 polylinker remaining in pHPT100. This construct was designated as pHPT102. The primers used to amplify the pgk promoter (Vanhanen, Saloheimo, Ilmen, Knowles and Penttila, "Promoter structure and expression of the 3-phosphoglycerate kinase gene (pgk1) of *Trichoderma reesei*", Gene 106: 129–133, 1991) were designed to introduce an XhoI site and a SphI site at positions −970 and +1 of the promoter respectively. These sites were subsequently used to insert the pgk promoter into the XhoI and SphI sites of pHPT102 to generate pHPT115. A 1.3 kb cbh1 terminator fragment was amplified with Pwo polymerase from pCB1Ta using a primer annealing to the 3' untranslated region of cbh1 (bp 1864–1899 of the published cbh1 sequence) containing a KpnI site at bp1877–1882 and the pUC reverse primer (Cat. No., 18432-013, Gibco/BRL) which anneals downstream of the EcoRI site at the 3' end of the cbh1 terminator in pCB1Ta. The cbh1 terminator PCR product was digested with KpnI and inserted into the unique KpnI site of pHPT115 to generate the selection cassette plasmid pHPT136.

To make the transformation vector, the expression cassette from pCBG1-Xho was isolated as a 5.6 kb Xba1/Xho1 fragment and inserted between the unique XbaI and XhoI sites upstream of the selection cassette of pHPT136. The final transformation vector, pCBG1-TV, as depicted in FIG. 1, was introduced as a circular plasmid into *T. reesei* M2C38 via microprojectile bombardment as described below in Example 9.

EXAMPLE 6

Construction of β-glucosidase Overexpression Vector pXBG1-TV

This Example describes the construction of a vector containing the Trichoderma xylanase II promoter and secretion signal, and the mature beta-glucosidase coding region.

The β-glucosidase coding region (bp 474–2680) was amplified with Pwo polymerase from the genomic bgl1 clone pJEN200 using primer to insert a XbaI site directly upstream of bp 474 in the published bgl1 sequence (Barnett, et al.) and a KpnI site directly downstream of bp 2680. The blunt ended PCR product was inserted into the SmaI site of pUC118 to generate the plasmid designated as pBGm.s. Since the XbaI site was engineered to be immediately upstream of the start of the mature β-glucosidase at Val32, the cloned fragment did not include the β-glucosidase secretion signal. The plasmid pBGm.s was digested with XbaI and KpnI and the 2.2 kb fragment containing the bgl1 coding region minus the secretion signal was isolated and inserted into the XbaI and KpnI sites upstream of the cbh2 terminator in the plasmid pCB219N (described in Example 5, above) to yield the plasmid pBG2X. A 2.3 kb fragment containing the promoter and secretion signal of the xln2 gene (bp −2150 to +99 where +1 indicates the ATG start codon) was amplified with Pwo polymerase from the genomic xln2 subclone pXYN2K-2 using a xln2-specific primer containing a NheI site directly downstream of bp103 of the published xln2 sequence (Saarelainen et al.) and the pUC reverse primer (Cat. No. 18432-013, Gibco/BRL) which anneals upstream of the KpnI site at the 5' end of the xln2 gene. This xln2 PCR product was digested with EcoRI (which was amplified as part of the pUC119 polylinker from pXYN2K-2) and NheI and inserted into the plasmid pBR322L (described in example 5 above) to generate pBR322LXN. The EcoRI site of pBR322LXN was then blunted with Klenow, and SpeI linkers (Cat. No. 1086, New England Biolabs) were added to generate pBR322SpXN. The pBG2X plasmid was cut with XbaI and NotI and a 4.2 kb fragment, containing the bgl1 coding region followed by the cbh2 terminator, was isolated. This fragment was inserted into the plasmid pBR322SpXN cut with NheI and NotI (NheI and XbaI have compatible overhangs). This cloning resulted in the fusion of the xylanase secretion signal directly to the mature β-glucosidase creating the complete expression cassette pXBG-2.

The cbh1 terminator in the selection cassette plasmid pHPT136 described in Example 5, above, was replaced with a 2.6 kb KpnI fragment containing the xln2 transcriptional terminator. The xln2 terminator was amplified with Pwo polymerase from the genomic subclone pXYN2K-2 using a primer to introduce a KpnI site directly downstream of bp 780 of the published xln2 sequence (Saarelainen et al.) and the pUC forward primer (Cat. No. 18431-015, Gibco/BRL) which anneals downstream of the 3' end of the xln2 gene in pXYN2K-2. The xln2 terminator PCR product was digested with KpnI and ligated to a 5.1 kb KpnI fragment from pHPT136 containing the pgk promoted-hph gene in pUC119 to generate the selection cassette plasmid pHPT136X.

The construction of the transformation vector involved the insertion of the expression cassette directly upstream of the pgk promoter from the selection cassette. The expression cassette plasmid pXBG2 was digested with NotI, the ends were made blunt using Klenow, and then digested with SpeI. The selection cassette pHPT136X was prepared in a similar manner by digestion with XhoI, followed by the fill in reaction to create the blunt ends and then a digestion with XbaI. A blunt-sticky ligation of these two fragments was performed to ligate the 6.5 kb SpeI/blunted NotI fragment from pXBG2 into the XbaI/blunted XhoI fragment of pHPT136X (SpeI and XbaI have compatible overhangs). The final transformation vector, pXBG-TV, as depicted in FIG. 2, was linearized at its unique NotI prior to transformation of T. reesei M2C38 via microprojectile bombardment, as described below in Example 9.

EXAMPLE 7

Construction of β-glucosidase Overexpression Vector pC/XBG(Xba1)-TV

This Example describes the construction of a vector containing the Trichoderma cellobiohydrolase 1 promoter, the xylanase II secretion signal and the mature beta-glucosidase coding region.

This Example was carried out to test the combined effects of the cbh1 promoter and xln2 secretion signal on bgl expression. A 1.2 kb HindIII fragment comprising bp −1399 to −204 of the cbh1 promoter was amplified by PCR using the cbh1 promoter-containing plasmid pBR322LCS (Example 5) as a template in order to insert a unique XbaI site at bp −1393 to −1388. This modified cbh1 promoter fragment was digested with HindIII and was used to replace bp −1400 to −121 of the xln2 promoter in pXBG1 (Example 6) to generate the new expression cassette plasmid pC/XBG1. The 6.4 kb expression cassette from pC/XBG1 was isolated by digestion with NotI followed by blunting of the NotI site with Klenow fragment and subsequent digestion with SpeI. This fragment was then inserted by blunt/sticky ligation upstream of the hph selection cassette in pHPT136X which had been digested with XhoI, blunted at the XhoI site with Klenow and digested with XbaI. The final transformation vector, pC/XBG(Xba1)-TV (Accession No. 209613, deposit date Feb. 3, 1998, American Type Culture Collection, 12301 Parklawn Drive, Rockville, Md. 20852 USA), as shown in FIG. 3, was linearized at the unique XbaI and NotI sites at the 5' end of the cbh1 promoter and the 3' end of the xln2 terminator prior to transformation of T. reesei M2C38 via microprojectile bombardment, as described below in Example 9.

EXAMPLE 8

Southern Blots of Genomic DNA Isolated from T. reesei Strains RutC30 and M2C38

Figure 5:
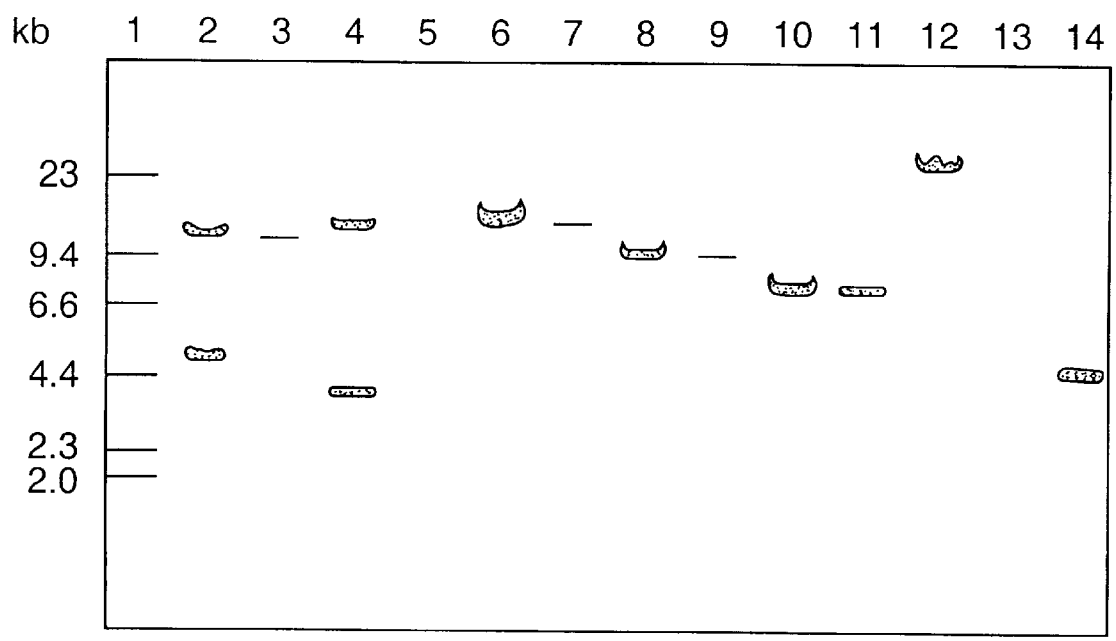
FIG. 5: Southern blot of genomic DNA isolated from *T. reesei* strains RutC30 and M2C38 and probed with a labeled DNA fragment comprising the M2C38 mature beta-glucosidase coding region.

Genomic DNA was isolated from each strain as described in Example 1. For Southern blots, 1 μg of DNA was digested with 3–10 units of restriction endonuclease at 37° C. for at least 2 hours and the digestion products resolved on a 0.8% agarose gel in 0.04 M Tris-acetate, 1 mM EDTA. DNA was transferred by nylon membranes (Boehringer Mannheim) by capillary transfer (Sambrook et al., pp. 9.38–9.44). In FIGS. 4 and 5, lanes 2, 4, 6, 8, 10 and 12 contain digested M2C38 DNA and lanes 3, 5, 7, 9, 11 and 13 contain digested RutC30 DNA. The restriction endonucleases used were BamHI (lanes 2 and 3), EcoRI (lanes 4 and 5), XbaI (lanes 6 and 7), Hind III (lanes 8 and 9), SstI (lanes 10 and 11) and KpnI (lanes 12 and 13). In both figures, lane 1 contains lambda-HindIII molecular size standards (Gibco/BRL, cat. no. 15612-013) and lane 14 contains 1 ng of unlabeled fragment used to make the probe. Southern blots were hybridized with a digoxigen-11-dUTP labelled random-primed probe prepared using the DIG Labeling and Detection Kit (Boehringer Mannheim). The template for the probe used in FIG. 4 was a 2.3 kb fragment comprising the T. reesei xln2 promoter and secretion signal (Saarelainen et al.). The template for the probe used in FIG. 5 was a 2.1 kb fragment comprising bp 574–2679 of the T. reesei bgl1 mature coding region (Barnett, et al.). After post-hybridization washes, dig-dUTP complexes were visualized by incubation with an anti-digoxigenin alkaline phosphatase conjugate (Boehringer Mannheim) followed by reaction with 5-bromo-4-chloro-3-indoyl phosphate and 4-nitro blue tetrazolium chloride (Boehringer Mannheim).

EXAMPLE 9

Transformation of T. reesei RutC30, M2C38 and BTR48 via Microprojectile Bombardment The Biolistic PDS-1000/He system (BioRad; E.I. DuPont de Nemours and Company) was used to transform spores of T. reesei strains RutC30, M2C38 and BTR48, and all procedures were performed as recommended by the manufacturer. M-10 tungsten particles (median diameter of 0.7 μm) were used as microcarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. Plates were prepared with $1 \times 10^6$ spores on Potato Dextrose Agar media (PDA). Bombarded plates were incubated at 28° C. Four hours post-bombardment, spores are subjected to primary selection by the overlaying of selective PDA media supplemented with 80 units/ml of HygB. The bombardment plates are incubated at 28° C. Transformants can be observed after 3–6 days growth; however, further incubation is necessary to achieve sporulation.

After sporulation has occurred, a secondary selection process is performed to isolate individual transformants. Spores are collected from the plate with an inoculating loop and resuspended in sterile water. This suspension is then filtered through a sterile syringe plugged with glass microfibers. This allows the passage of spores while retaining unwanted mycelia. A determination of the concentration of spores in this suspension is required and subsequent dilutions are plated onto PDA plates supplemented with 0.75% Oxgall (Difco) and HygB (40 units/mL) to obtain 20–50 spores per plate. The Oxgall acts as a colony restrictor, thereby allowing the isolation of individual colonies on these secondary selection plates. Isolated colonies can be observed after 2–3 days.

EXAMPLE 10

Southern Blot Analysis of Genomic DNA Isolated from T. reesei Strains RutC30, RC300, RC-302, M2C38, RM4-300, R4-301, RM4-302, BTR48, and RB4-301

Genomic DNA was isolated from each strain as described in Example 1. For Southern blots, 1 μg of DNA was digested with 3–10 units of Kpn1 or Xba1 at 37° C. for at least 2 hours and the digestion products resolved on a 0.8% agarose gel in 0.04 M Tris-acetate, 1 mM EDTA. DNA was transferred by nylon membranes (Boehringer Mannheim) by capillary transfer (Sambrook et al., pp. 9.38–9.44). Southern blots were hybridized with a digoxigen-11-dUTP labelled random-primed probe prepared using the DIG Labeling and Detection Kit (Boehringer Mannheim). The template was a 1.3 kb EcoR1-Bgl II fragment comprising bp1215–2464 of the published bgl1 sequence (Barnett et al.). After post-hybridization washes, dig-dUTP complexes were visualized by incubation with an anti-digoxigenin alkaline phosphatase conjugate (Boehringer Mannheim) followed by reaction with the chemiluminescent reagent CSPD (Boehringer Mannheim) and exposure to X-ray film (Kodak). The results are summarized in Table 1.

TABLE 1 bgl1 copy number in parental and recombinant T. reesei strains

| Strain | Host | Promoter | Secretion signal | Vector | native bgl1 gene | # bgl1 vectors | total # bgl1 genes |
|---|---|---|---|---|---|---|---|
| RutC30 | Same | bgl1 | bgl1 | none | Present | 0 | 1 |
| RC-300 | RutC30 | cbh1 | cbh1 | pCBG1-TV | Present | 1 | 2 |
| RC-302 | RutC30 | cbh1 | xln2 | pC/XBG1-TV | Absent | 1 | 1 |
| M2C38 | Same | bgl1 | bgl1 | None | Present | 0 | 1 |
| RM4-300 | M2C38 | cbh1 | cbh1 | pCBG1-TV | Absent | 2 | 2 |
| RM4-301 | M2C38 | xln2 | xln2 | pXBG1-TV | Present | 2 | 3 |
| RM4-302 | M2C38 | cbh1 | xln2 | pC/XBG1-TV | Present | 2 | 3 |
| BTR48 | Same | bgl1 | bgl1 | None | Present | 0 | 1 |
| RB4-301 | BTR48 | xln2 | xln2 | pXBG1-TV | Absent | 2 | 2 |

EXAMPLE 11

Production of β-glucosidase in Liquid Cultures

This Example describes the methods used to determine the amount of beta-glucosidase enzyme produced by a Trichoderma strain.

Individual colonies of Trichoderma are transferred to PDA plates for the propagation of each culture. Sporulation is necessary for the uniform inoculation of shake flasks which are used in testing the ability of the culture to produce the beta-glucosidase and cellulase. The culture media is composed of the following:

| Component | g/L |
|---|---|
| $(NH_4)_2SO_4$ | 6.35 |
| $KH_2PO_4$ | 4.00 |
| $MgSO_4-7H_2O$ | 2.02 |
| $CaCl_2-2H_2O$ | 0.53 |
| CSL | 6.25 |
| $CaCO_3$ | 10.00 |
| Carbon sources** | 5–10 |
| Trace elements* | 1 mL/L |

The liquid volume per 1-liter flask is 150 mL, the initial pH is 5.5 and each flask is sterilized by steam autoclave for 30 minutes at 121° C. prior to inoculation.

For both untransformed (i.e., native) and transformed cells, spores are isolated from the PDA plates as described in Example 9 and $1-2 \times 10^6$ spores are used to inoculate each flask. The flasks are shaken at 200 rpm at a temperature of 28° C. for a period of 6 days. The filtrate containing the secreted protein was collected by filtration through GF/A glass microfibre filters (Whatman). The protein concentration is determined using the Bio-Rad Protein Assay (Cat. No. 500-0001) using Trichoderma cellulase as a standard. Beta-glucosidase activity is determined as described in Example 16.

Transformants were screened for the ability to produce at least 10-fold more beta-glucosidase (in IU/mg) than the untransformed host strain as determined by the IU/ml of beta-glucosidase activity of the culture filtrate divided by the protein concentration (in mg/ml) of the culture filtrate.

EXAMPLE 12

Production of Beta-glucosidase by *T. reesei* strains RutC30, RC-300, and RC-302 using Solka floc Carbon Source Based on previous successes using the cbh1 promoter and secretion signal to overexpress proteins in Trichoderma, the mature beta-glucosidase coding region was placed downstream of the cbh1 promoter and secretion signal in the genetic construct shown in FIG. 1 and described in Example 5 (pCBG1-TV). The vector was introduced into *T. reesei* RutC30 by particle bombardment (Example 9) and the resulting transformant RC-300, produced 7 times more beta-glucosidase activity than the parental strain (Table 2). This 7-fold increase resulted from the incorporation of one copy of the transformation vector into the host chromosomes (Example 10, Table 1). The larger increase in beta-glucosidase activity obtained from one copy of a construct in which beta-glucosidase is expressed using the cbh1 promoter and secretion signal suggests that this strategy is better than that employed by Barnett et al. and Fowler et al. which resulted in only a 5-fold increase in beta-glucosidase activity from 10–15 copies of a construct in which beta-glucosidase is expressed from its own promoter and secretion signal. However, the resulting 7-fold increase in beta-glucosidase activity was still not sufficient to alleviate the shortage of beta-glucosidase for cellulose hydrolysis.

The untransformed *T. reesei* strain RutC30 was transformed by particle bombardment (Example 9) with a genetic construct from the vector pC/XBG(Xba1)-TV encoding the mature *T. reesei* beta-glucosidase enzyme linked to the *T. reesei* xylanase II secretion signal.

The untransformed strain RutC30 and the resulting transformed strain from this host, RC-302, were cultured using the procedures of Example 11 with 10 g/L Solka floc and 5 g/L glucose as carbon sources. The results are shown in Table 2. The untransformed strain produced 0.14 IU of beta-glucosidase per mg protein.

The transformant RC-302 with the CBH1 promoter and xylanase II secretion signal produced 19 IU/mg of beta-glucosidase. This represents about a 136-fold improvement over the untransformed strain, which is very significant for a cellulose-to-ethanol process.

The transformant RC-302 with the CBH1 promoter and xylanase II secretion signal produced about 19 times more beta-glucosidase activity than the best RutC30 transformant with the CBH1 promoter and CBH1 secretion signal.

TABLE 2

Production of β-glucosidase in *T. reesei* strains RutC30, RC-300, and RC-302 in 150 ml flask cultures

| Strain | promoter | Secretion signal | β-g (IU/mg) |
| --- | --- | --- | --- |
| RutC30 | bgl1 | bgl1 | 0.14 |
| RC-300 | cbh1 | cbh1 | 1.0 |
| RC-302 | cbh1 | xln2 | 19 |

EXAMPLE 13

Production of Beta-glucosidase by Strains M2C38 and RM4-302 Using Solka floc Carbon Source The vector pCBG1-TV, in which the beta-glucosidase is expressed from the CBH1 promoter and secretion signal (FIG. 1 and Example 5), was introduced into *T. reesei* M2C38 by particle bombardment (Example 9). The resulting transformant RM4-300 produced about 7–12 times more beta-glucosidase activity than the parental strain (Table 3).

The untransformed *T. reesei* strain M2C38 was transformed by particle bombardment (Example 9) with a genetic construct from the vector pC/XBG(Xba1)-TV encoding the mature *T. reesei* beta-glucosidase enzyme linked to *T. reesei* xylanase II secretion signal.

The untransformed strain M2C38 and the transformed strain from this host, RM4-302, were cultured using the procedures of Example 11 with 10 g/L Solka floc and 5 g/L glucose as carbon sources. The results are shown in Table 3.

The untransformed strain produced 0.35 IU of beta-glucosidase per mg protein.

The transformant RM4-302 with the CBH1 promoter and xylanase II secretion signal produced 14.1 IU/mg of beta-glucosidase. This represents about a 40-fold improvement over the untransformed strain, which is very significant for a cellulose-to-ethanol process.

The transformant RM4-302 with the CBH1 promoter and xylanase II secretion signal produced about 3 times more beta-glucosidase activity than the transformant with the CBH1 promoter and CBH1 secretion signal. This is a significant difference, as the CBH1 promoter and secretion signal did not lead to sufficient production of beta-glucosidase to completely suppress cellobiose production in hydrolysis.

TABLE 3

Production of β-glucosidase in *T. reesei* strains M2C38, RM4-300, and RM4-302 in 150 ml flask cultures

| Strain | promoter | Secretion signal | β-g (IU/mg) |
| --- | --- | --- | --- |
| M2C38 | bgl1 | bgl1 | 0.35 |
| RM4-300 | cbh1 | cbh1 | 4.5 |
| RM4-302 | cbh1 | xln2 | 14.1 |

EXAMPLE 14

Production of Beta-glucosidase by *T. reesei* Strains M2C38 and RM4-301 Using Xylan Carbon Source The untransformed *T. reesei* strain M2C38 was transformed by particle bombardment (Example 9) with a genetic construct from the vector pXBG1-TV encoding the mature *T. reesei* beta-glucosidase linked to the xylanase promoter and secretion signal.

The untransformed strain M2C38 and a transformed strain from this host, RM4-301, were cultured using the procedures of Example 11 with 5 g/L glucose and 10 g/L xylan as the carbon source. The results are shown in Table 4.

The untransformed strain produced 0.16 IU of beta-glucosidase per mg protein. The transformant RM4-301 with the xylanase II promoter and xylanase II secretion signal produced 20.4 IU/mg of beta-glucosidase. This represents about a 127-fold improvement over the untransformed strain, which is very significant for a cellulose-to-ethanol process.

TABLE 4

Production of β-glucosidase in *T. reesei* strains M2C38 and RM4-301 with xylan in 150 ml flask cultures

| Strain | promoter | Secretion signal | β-g (IU/mg) |
|---|---|---|---|
| M2C38 | bgl1 | bgl1 | 0.16 |
| RM4-301 | xln2 | xln2 | 20.4 |

EXAMPLE 15

Production of Beta-glucosidase by Strains BTR-48 and RB48-301 Using Solka floc Carbon Source The untransformed *T. reesei* strain BTR48 was transformed by particle bombardment with a genetic construct from the vector pXBG1-TV encoding the mature *T. reesei* beta-glucosidase linked to the xylanase promoter and secretion signal.

The untransformed strain BTR-48 and a transformed strain from this host, RB48-301, were cultured using the procedures of Example 11 with 5 g/L glucose and 10 g/L Solka floc as the carbon sources. The results are shown in Table 5.

The untransformed strain produced 0.16 IU of beta-glucosidase per mg protein. The transformant RB48-301 with the xylanase II promoter and xylanase II secretion signal produced about 21.9 IU/mg of beta-glucosidase. This represents about a 136-fold improvement over the untransformed strain, which is very significant for a cellulose-to-ethanol process.

TABLE 5

Production of β-glucosidase in *T. reesei* strains BTR48 and RB48-301 with Solka floc in 150 ml flask cultures

| Strain | promoter | Secretion signal | β-g (IU/mg) |
|---|---|---|---|
| BTR48 | bgl1 | bgl1 | 0.16 |
| RB48-301 | xln2 | xln2 | 21.9 |

EXAMPLE 16

Measurement of Beta-glucosidase Activity of an Enzyme Mixture

The beta-glucosidase activity of an enzyme is measured using the procedures of Ghose, "Measurement of Cellulase Activities," Pure and Appl. Chem., 59:257–268 (1987), as follows. The sample of enzyme is diluted to several concentrations in 50 mM sodium citrate buffer, pH 4.8, to a volume of 0.5 ml. A convenient range of dilutions is 3 to 24 times the estimated activity of the sample. For example, a 10 unit/ml sample should be diluted 1:30 to 1:240. Regardless of the dilutions used, a sample of 0.5 ml of the citrate buffer is added to each enzyme tube. The substrate is prepared as 15 mM (5.13 g/L) cellobiose. The dilute enzyme stocks and the substrate are separately preheated to 50° C. for 5 minutes, then a 0.5 ml aliquot of the substrate is added to each tube with enzyme. The test tubes are incubated for 30 minutes at 50° C. The reaction is terminated by immersing each tube in a boiling water bath for 5 minutes. The tubes are then vortex mixed, and the amount of sugar produced by each sample of enzyme is measured on a YSI glucose analyzer, taking into account the small background from the enzyme.

A unit of beta-glucosidase activity is defined as the number of micromoles of glucose produced per minute. The activity is calculated based on Equation 1 using the average value from each of the dilutions which produces 0.15 to 1.5 mg/ml of glucose.

$$A = C*G*D \tag{1}$$

where A=activity, beta-glucosidase units/ml (or micromoles glucose/ml/min)
C=16.7 micromoles/mg/min
G=glucose produced, mg/ml
D=enzyme dilution, dimensionless

EXAMPLE 17

Cellulose Hydrolysis

The purpose of this experiment was to demonstrate the effectiveness of the beta-glucosidase made by the transformed Trichoderma in enhancing the hydrolysis of cellulose.

The enzymes used for this study were Iogen Cellulase, a commercial cellulase enzyme of Iogen Corporation, and the product of RM4-302 grown in a 30-liter fermentation vessel using the procedures described in Example 11, with twice the media concentration levels listed in that Example. The enzyme concentration was increased by ultrafiltration across an Amicon 10,000 MWCO membrane and normalized to the same cellulase activity as Iogen Cellulase. The activities of these two enzymes are shown in Table 6.

TABLE 6

Enzyme activities used in cellulose hydrolysis study

| Enzyme | Beta-glucosidase IU/ml | Cellulase FPU/ml | BG IU/mg @ 10 FPU/g |
|---|---|---|---|
| Iogen Cellulase | 112 | 140 | 8.0 |
| RM4-301 | 1170 | 140 | 83.6 |

The cellulose used for this study was pretreated oat hulls, prepared as per the procedures of Foody, et al, Improved Pretreatment Process for Conversion of Cellulose to Fuel Ethanol, US patent application filed Jun. 9, 1997, Example 6.

Samples of pretreated oat hull cellulose of 0.5 grams were added to 25 ml flasks with 49.5 grams of 0.05 molar sodium citrate buffer, pH 4.8.

The enzymes were added to the flask in an amount corresponding to 10 FPU per gram of cellulose. The resulting beta-glucosidase dosages are listed in Table 6.

In both cases, the flasks were shaken at 250 RPM and maintained at 50° C. for 24 hours. At this time, samples were taken, filtered to remove insoluble cellulose, and analyzed for glucose and cellobiose concentration using standard Dionex pulsed-amperometric HPLC carbohydrate analysis methods. The results are listed in Table 7.

Iogen Cellulase, the conventional Trichoderma cellulase, converted only 45% of the cellulose to glucose. This is unacceptably low for an ethanol process. The accumulation of cellobiose was significant, representing 13% of the cellulose.

The cellulase with enhanced beta-glucosidase performed much better. The cellulose conversion to glucose reached 84%. The reason for this excellent performance was that cellobiose accumulation was negligible, due to the abundance of beta-glucosidase.

TABLE 7

Hydrolysis of cellulose enhanced by high beta-glucosidase

| Enzyme | Glucose (% of cellulose) | Cellobiose (% of cellulose) |
|---|---|---|
| Iogen Cellulase | 45 | 13 |
| RM4-301 | 84 | <1 |

EXAMPLE 18

Comparison of the *Trichoderma reesei* xln2 and bgl1 Genes in Strains RutC30 and M2C38

Southern Blot analysis was performed on M2C38 and RutC30 DNA digested with six different restriction enzymes that cut both within and outside of the regions that encode the mature beta-glucosidase and the xylanase secretion signal (Example 8) to determine if any polymorphisms exist between the two strains. As shown in FIGS. 4 and 5, the identical bands were found to hybridize with labelled probes prepared from M2C38 fragments encoding the mature beta-glucosidase enzyme and the xylanase II promoter plus secretion signal, indicating no polymorphisms and a high degree of DNA sequence homology in these regions between the two strains.

The probes and primers used to identify and clone the M2C38 DNA sequences necessary to make the genetic constructs described in Examples 5–7 were based on published DNA sequences of the various genes from several different *Trichoderma reesei* strains including QM9414 (pgk, Vanhanen et al., 1989 and cbh2, Chen et al.), the QM9414 derivatives VTT-D79125 (xln2, Saarelainen et al.) and L27 (cbh1, Shoemaker et al.), and the strain RL-P37 derivative strain P40 (bgl1, Barnett et al.). All of these strains, like M2C38, are derived from strain QM6a (Carter, Allison, Rey and Dunn-Coleman, "Chromosomal and genetic analysis of the electrophoretic karyotype of *Trichoderma reesei:* mapping of the cellulase and xylanase genes," Molecular Microbiology 6: 2167–2174, 1992).

Because RutC30 is the QM6a-derived progenitor of M2C38, the inventors are confident that the method as described in Examples 2–4, for the isolation of the gene sequences used to make the beta-glucosidase expression vectors described in Examples 5–7, will work equally well for the isolation of the same gene sequences from both M2C38 and RutC30. Based on the strain lineage described above and the Southern blot data, the inventors also have a high degree of confidence that genetic constructs prepared from RutC30 DNA will contain the identical DNA segments encoding the mature beta-glucosidase enzyme and the xylanase II secretion signal as those prepared from M2C38 DNA. Since the constructs prepared from M2C38 DNA (Examples 5–7) result in enhanced beta-glucosidase expression in both M2C38 and RutC30 (Examples 12–14), the inventors are also confident that genetic constructs made from RutC30 DNA will result in similar levels of enhancement of beta-glucosidase activity in both RutC30 and M2C38.

While the present invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. A genetically modified microbe comprising:
   a microbe selected from the group consisting of Trichoderma, Humicola, Fusarium, and Aspergillus; and
   a genetic construct that has been introduced into said microbe, said genetic construct having a promoter selected from the group consisting of cbh1, cbh2, eg1, eg2, eg3, eg5, xln1 and xln2,
   a xylanase secretion signal, and
   a mature beta-glucosidase coding region,
   wherein said genetically modified microbe produces an increased level of beta-glucosidase relative to said microbe.

2. The genetically modified microbe of claim 1, wherein said microbe is a Trichoderma microbe.

3. The genetically modified microbe of claim 2, wherein said Trichoderma microbe is a *Trichoderma reesei* microbe.

4. The genetically modified microbe of claim 1, wherein said genetically modified microbe produces an increased level of beta-glucosidase of at least about 10-fold.

5. The genetically modified microbe of claim 1, wherein said genetically modified microbe produces an increased level of beta-glucosidase of at least about 40-fold.

6. The genetically modified microbe of claim 1, wherein said genetically modified microbe produces an increased level of beta-glucosidase of at least about 120-fold.

7. The genetically modified microbe of claim 1, wherein said xylanase secretion signal is native to said microbe from which said genetically modified microbe is derived.

8. The genetically modified microbe of claim 1, wherein said xylanase secretion signal comprises a xylanase secretion signal of a Family 11 xylanase gene.

9. The genetically modified microbe of claim 8, wherein said Family 11 xylanase gene comprises a Trichoderma xylanase gene.

10. The genetically modified microbe of claim 9, wherein said Trichoderma xylanase gene comprises a *Trichoderma reesei* xylanase I gene or a Trichoderma xylanase II gene.

11. The genetically modified microbe of claim 1, wherein said mature beta-glucosidase coding region comprises a mature beta-glucosidase coding region of a Trichoderma beta-glucosidase gene.

12. The genetically modified microbe of claim 2, wherein said mature beta-glucosidase coding region comprises a mature beta-glucosidase coding region of a Trichoderma beta-glucosidase gene.

13. The genetically modified microbe of claim 3, wherein said mature beta-glucosidase coding region comprises a mature beta-glucosidase coding region of a Trichoderma beta-glucosidase gene.

14. The genetically modified microbe of claim 4, wherein said mature beta-glucosidase coding region comprises a mature beta-glucosidase coding region of a Trichoderma beta-glucosidase gene.

15. The genetically modified microbe of claim 5, wherein said mature beta-glucosidase coding region comprises a mature beta-glucosidase coding region of a Trichoderma beta-glucosidase gene.

16. The genetically modified microbe of claim 6, wherein said mature beta-glucosidase coding region comprises a mature beta-glucosidase coding region of a Trichoderma beta-glucosidase gene.

17. The genetically modified microbe of claim 7, wherein said mature beta-glucosidase coding region comprises a mature beta-glucosidase coding region of a Trichoderma beta-glucosidase gene.

18. The genetically modified microbe of claim 8, wherein said mature beta-glucosidase coding region comprises a mature beta-glucosidase coding region of a Trichoderma beta-glucosidase gene.

19. The genetically modified microbe of claim 9, wherein said mature beta-glucosidase coding region comprises a mature beta-glucosidase coding region of a Trichoderma beta-glucosidase gene.

20. The genetically modified microbe of claim 10, wherein said mature beta-glucosidase coding region comprises a mature beta-glucosidase coding region of a Trichoderma beta-glucosidase gene.

21. A genetic construct comprising:
    a promoter selected from the group consisting of cbh1, cbh2, eg1, eg2, eg3, eg5, xln1, and xln2 promoters;
    a xylanase secretion signal of a Family 11 xylanase gene; and
    a mature beta-glucosidase coding region of a beta-glucosidase gene selected from the group consisting of Trichoderma, Aspergillus, Humicola, and Fusarium beta-glucosidase genes.

22. The genetic construct of claim 21, wherein said Family 11 xylanase gene comprises a Trichoderma xylanase gene.

23. The genetic construct of claim 22, wherein said Trichoderma xylanase gene comprises a *Trichoderma reesei* xylanase I gene or a *Trichoderma reesei* xylanase II gene.

24. The genetic construct of claim 21, wherein said mature beta-glucosidase coding region comprises a mature beta-glucosidase coding region of a Trichoderma beta-glucosidase gene.

25. The genetic construct of claim 24, wherein said Trichoderma beta-glucosidase gene comprises a *Trichoderma reesei* bglI gene.

26. A method of producing beta-glucosidase, comprising:
transforming a microbe selected from the group consisting of Trichoderma, Aspergillus, Humicola, and Fusarium with a genetic construct comprising a promoter selected from the group consisting of cbh1, cbh2, eg1, eg2, eg3, eg5, xln1 and xln2,
a xylanase secretion signal, and
a mature beta-glucosidase coding region, to create a genetically modified microbe; and
using the genetically modified microbe to produce an increased level of beta-glucosidase relative to the microbe prior to being transformed.

27. The method of claim 26, wherein said using step comprises using the genetically modified microbe to produce an increased level of beta-glucosidase of at least about 10-fold.

28. The method of claim 26, wherein said using step comprises using the genetically modified microbe to produce an increased level of beta-glucosidase of at least about 40-fold.

29. The method of claim 26, wherein said using step comprises using the genetically modified microbe to produce an increased level of beta-glucosidase of at least about 120-fold.

* * * * *